US012589129B2

(12) United States Patent
Sardeshmukh et al.

(10) Patent No.: US 12,589,129 B2
(45) **Date of Patent: \*Mar. 31, 2026**

(54) POLYHERBAL METALLO-MINERAL PHARMACEUTICAL KIT

(71) Applicant: Sadanand Prabhakar Sardeshmukh, Pune (IN)

(72) Inventors: Sadanand Prabhakar Sardeshmukh, Pune (IN); Vineeta Vasant Deshmukh, Pune (IN)

(73) Assignee: Sadanand Sardeshmukh, Pune (IN)

( * ) Notice: Subject to any disclaimer, the term of this patent is extended or adjusted under 35 U.S.C. 154(b) by 502 days.

This patent is subject to a terminal disclaimer.

(21) Appl. No.: 18/015,577

(22) PCT Filed: Jul. 13, 2021

(86) PCT No.: PCT/IB2021/056285
§ 371 (c)(1),
(2) Date: Jan. 11, 2023

(87) PCT Pub. No.: WO2022/013731
PCT Pub. Date: Jan. 20, 2022

(65) Prior Publication Data
US 2023/0248793 A1      Aug. 10, 2023

(30) Foreign Application Priority Data
Jul. 15, 2020    (IN) .............................. 202021030193

(51) Int. Cl.
| | |
|---|---|
| *A61K 36/484* | (2006.01) |
| *A61K 33/242* | (2019.01) |
| *A61K 35/618* | (2015.01) |
| *A61K 36/00* | (2006.01) |
| *A61K 36/185* | (2006.01) |
| *A61K 45/06* | (2006.01) |
| *A61K 47/44* | (2017.01) |

(52) U.S. Cl.
CPC .......... *A61K 36/484* (2013.01); *A61K 33/242* (2019.01); *A61K 35/618* (2013.01); *A61K 36/185* (2013.01); *A61K 47/44* (2013.01)

(58) Field of Classification Search
CPC .. A61K 36/484; A61K 33/242; A61K 35/618; A61K 36/185; A61K 47/44; A61K 45/06; A61K 36/00; A61K 2300/00
See application file for complete search history.

(56) References Cited

U.S. PATENT DOCUMENTS

| | | | | |
|---|---|---|---|---|
| 12,201,660 | B2 * | 1/2025 | Sardeshmukh | ........... A61P 1/08 |
| 2022/0211753 | A1 * | 7/2022 | Sardeshmukh | ........ A61K 36/53 |
| 2022/0211794 | A1 * | 7/2022 | Sardeshmukh | ...... A61K 36/736 |
| 2022/0226419 | A1 * | 7/2022 | Sardeshmukh | ........ A61K 47/36 |
| 2023/0233601 | A1 * | 7/2023 | Sardeshmukh | ...... A61K 9/2072 |
| | | | | 424/547 |
| 2024/0165190 | A1 * | 5/2024 | Sardeshmukh | ........ A61K 36/67 |

OTHER PUBLICATIONS

RS22/165, Svarna Bhasma Anupana, Knowledge known since 50 years the Whole document.
VS/2521, Kmadudhrasa (Mauktikayuktam), Knowledge known since 50 years the Whole document.
AA3/1261, Dawa Saman Brae Waram-e-Hanjarah, Knowledge known since 1000 years the Whole document.
AT/1300, Mahsugandhlepa, Knowledge known since 1000 years the Whole document.
RG/2230, Madhuya°iprayogam, Knowledge known since 500 years the Whole document.
AK11/3823B, Haridradi Kvatha, Knowledge known since 500 years the Whole document.
International Search Report and Written Opinion of PCT/IB2021/056285 Completed Nov. 15, 2021; Mailed Nov. 15, 2021 7 pages.

\* cited by examiner

*Primary Examiner* — Mina Haghighatian
(74) *Attorney, Agent, or Firm* — The Roy Gross Law Firm, LLC; Roy D. Gross

(57) ABSTRACT

The present disclosure relates to the field of polyherbal metallo-mineral pharmaceutical kit. The kit of the present disclosure can be used for alleviating adverse effects of radiotherapy, reducing oxidative stress, and improving immunomodulatory response, oral hygiene and quality of life of the patients. The polyherbal metallo-mineral pharmaceutical kit comprises Suvarna bhasmadi Vati (SBV), Mouktikyukta Kamdudha Vati (MKV), Yashtimadhu Ghrut (YTG), Yashtimadhu Taila (YTO), Ananta Vati (AV) and Gandush Churna (GC).

13 Claims, 18 Drawing Sheets

POLYHERBAL METALLO-MINERAL PHARMACEUTICAL KIT

CROSS REFERENCE TO RELATED APPLICATIONS

This application is a National Phase of PCT Patent Application No. PCT/IB2021/056285 having International filing date of Jul. 13, 2021, which claims the benefit of priority of Indian Patent Application No. 202021030193, filed Jul. 15, 2020, the contents of which are all incorporated herein by reference in their entirety.

FIELD

The present disclosure relates to a polyherbal metallo-mineral pharmaceutical kit. Particularly, the present disclosure relates to a polyherbal metallo-mineral pharmaceutical kit for alleviating adverse effects of radiotherapy, and for improving the immunomodulatory response.

DEFINITIONS

As used in the present disclosure, the following terms are generally intended to have the meaning as set forth below, except to the extent that the context in which they are used to indicate otherwise.

Suvarna bhasma: The term "Suvarna bhasma" refers to "incinerated gold" prepared by incinerating gold in accordance with the present disclosure. The term "Suvarna" refers to 24 carat gold. The term "Suvarna bhasma" as is referred to in the present disclosure is not the same as used in the Ayurveda.

Mouktik bhasma: The term "Mouktik bhasma" refers to "incinerated pearl", natural or cultured, prepared by incinerating pearl in accordance with the present disclosure. The term "Mouktik bhasma" as referred to in the present disclosure is not the same as used in Ayurveda.

Guduchi Sattva: The term "Guduchi Sattva" refers to an alcoholic, hydro alcoholic or aqueous extract comprising mainly starch of *Tinospora cordifolia* or *Tinospora sinensis* or *Tinospora crispa* or *Tinospora glabra*. The term "Guduchi Sattva" as is referred to in the present disclosure is not the same as used in Ayurveda.

Yashtimadhu: The term "Yashtimadhu" refers to "Liquorice" or "*Glycyrrhiza glabra*".

Haritaki: The term "Haritaki" refers to "Chebulic myrobalan" or "*Terminalia chebula*".

Bibhitaki: The term "Bibhitaki" refers to "Belleric myrobalan" or "*Terminalia bellerica*".

Amalaki: The term "Amalaki" refers to "Indian gooseberry" or "*Phyllanthus emblica/Emblica officinalis*".

Haridra: The term "Haridra" refers to "Turmeric" or "*Curcuma longa*".

Ananta: The term "Ananta" refers to "Swallow root" or "*Decalepis hamiltonii/Hemidesmus indicus/Cryptolepis buchnani/Ichnocarpus frutescens.*"

Ghrut: The term "Ghrut" or "Ghee" refers to clarified butter produced from cow's milk.

Taila: The term "Taila" refers to "Sesame Oil".

Shankha bhasma: The term "Shankha bhasma" refers to "incinerated Conch shell". The term "Shankha bhasma" as is referred to in the present disclosure is not the same as used in Ayurveda.

Shouktik bhasma: The term "Shouktik bhasma" refers to "incinerated empty pearl shell". The term "Shouktik bhasma" as is referred to in the present disclosure is not the same as used in Ayurveda.

Kapardika bhasma: The term "Kapardika Bhasma" refers to "incinerated Cowries". The term "Kapardika Bhasma" as is referred to in the present disclosure is not the same as used in Ayurveda.

Pravala bhasma: The "Pravala Bhasma" refers to "incinerated coral". The term "Pravala Bhasma" as is referred to in the present disclosure is not the same as used in Ayurveda.

Shudhha Gairik: The "Gairik" is a natural clay earth pigment which is a mixture of ferric oxide and varying amounts of clay and sand. "Shudhha Gairik" refers to "processed Gairik", prepared by roasting Gairik in ghee obtained from cow's milk. The term "Gairik" as is referred to in the present disclosure is not the same as used in Ayurveda.

Vati: The term "Vati" refers to a method of medicine preparation in which herbs, minerals, and metallic compounds are compressed into tablet form.

Wick test: The term "wick test" refers to igniting a wick made out of residual solid part after separating Ghrut. Crackling sound of ignited wick indicates the presence of water.

Nasya: The term "Nasya" refers to nasal instillation.

Gandush: The term "Gandush" refers to gargling.

Karnofsky score: The term "Karnofsky score" refers to the Karnofsky Performance Scale Index, which allows patients to be classified according to their functional impairment.

QoL: QoL refers to the general Quality of Life

QLQ: QLQ refers to the Quality of Life Quotient

Symptom score: Symptom score of QLQ is indicative of symptomatology; hence decrease in symptom score represents both decrease in disease related symptoms and adverse effects of conventional treatment.

Functional score: Functional score of QLQ signifies status of routine physical activities. Increase in functional score represents improvement in QoL.

Global score: Global score of QLQ represents overall well-being of a patient. Increase in global score represents improvement in QoL.

Head and Neck Score: Head and Neck score of QLQ is indicative of local head and neck related symptomatology; hence decrease in symptom score represents decrease in disease related local symptoms and adverse effects of conventional treatment.

Decoction: Decoction is a method of extraction by boiling herbal or plant material to dissolve the chemicals of the material, which may include stems, stolons, roots, bark and rhizomes.

SGOT: Serum glutamic-oxaloacetic transaminase (SGOT), or Aspartate aminotransferase (AST), is an enzyme that is primarily found in the liver and heart. The SGOT is a blood test that helps to determine how well the liver is functioning. Too much of this enzyme can indicate a problem, such as liver damage.

SGPT: Serum glutamic-pyruvic transaminase (SGPT), or alanine transaminase (ALT), is an enzyme made in the liver. It is released into the blood when tissues are damaged. The SGPT is a blood test that checks for and measures damage to the liver.

BACKGROUND

The background information herein below relates to the present disclosure but is not necessarily prior art.

Oral cavity cancer ranks amongst the top three cancers in India. The recommended curative treatment for oral cancers is surgery followed by radiotherapy (RT) depending upon the stage of the disease. In addition, chemotherapy is recommended for enhancing the effect of radiation treatment and is accepted as a part of combined modality treatment, particularly in patients in stage III and IV of the disease. It is well known that both RT and chemotherapy have adverse side effects often leading to interruption in therapeutic schedule in these patients. Radiation induced side effects in oral cancer patients such as stomatitis, trismus, xerostomia, taste disturbance, fatigue etc. are well documented. These symptoms lead to increase in oxidative stress and hampered immune system.

Worldwide efforts have been made to address the question of alleviating side-effects of therapy so as to achieve uninterrupted therapy and to maintain the Quality of Life (QoL) especially in oral cancer patients as they are nutritionally deprived because of the location of the tumor.

Therefore, there is felt a need to provide a specific combination of polyherbal metallo-mineral compositions, in the form of a kit, that mitigates the aforestated problems.

OBJECTS

Some of the objects of the present disclosure, which at least one embodiment herein satisfies, are as follows.

An object of the present disclosure is to ameliorate one or more problems of the prior art or to at least provide a useful alternative.

Another object of the present disclosure is to provide a polyherbal metallo-mineral pharmaceutical kit.

Still another object of the present disclosure is to provide a polyherbal metallo-mineral pharmaceutical kit for alleviating adverse effects of radiotherapy.

Another object of the present disclosure is to provide a polyherbal metallo-mineral pharmaceutical kit for reducing oxidative stress, and improving the oral hygiene and immune response in patients treated with radiotherapy for improving the quality of life in patients.

Other objects and advantages of the present disclosure will be more apparent from the following description, which is not intended to limit the scope of the present disclosure.

SUMMARY

The present disclosure provides a polyherbal metallo-mineral pharmaceutical kit comprising a first container containing Suvarna Bhasmadi Vati (SBV) in solid dosage form in an amount in the range of 800 mg/day to 1000 mg/day; a second container containing Mouktikyukta Kamdudha Vati (MKV) in solid dosage form in an amount in the range of 800 mg/day to 1200 mg/day; a third container containing Yashtimadhu Ghrut (YTG) in thick, viscous dosage form in an amount in the range of 8 gm/day to 12 gm/day; a fourth container containing Ananta Vati (AV) in solid dosage form in an amount in the range of 0.5 gm/day to 2 gm/day; a fifth container containing Yashtimadhu Taila (YTO) in viscous oily dosage form in an amount in the range of 2 drop/day to 5 drops/day; and a sixth container containing Gandush Churna (GC) in coarse powder dosage form in an amount in the range of 3 gm/day to 10 gm/day.

BRIEF DESCRIPTION OF THE ACCOMPANYING DRAWING

The present disclosure will now be described with the help of the accompanying drawing, in which:

4

DETAILED DESCRIPTION

Figure 1A:
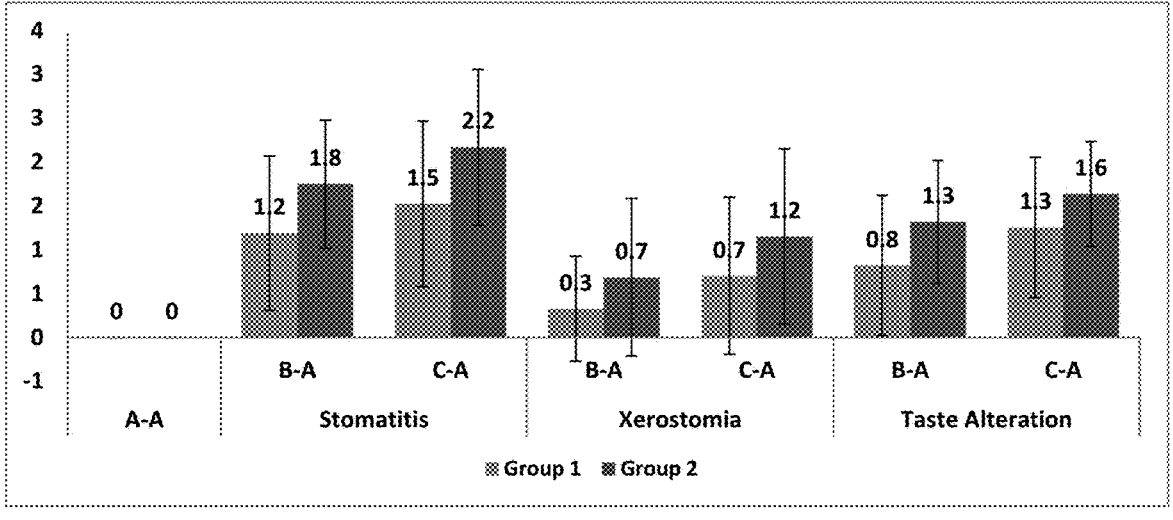
FIG. 1A depicts the clinical investigation for stomatitis, xerostomia and taste alteration in Study group denoted by 'Group 1' and Control group denoted by 'Group 2'.

Embodiments, of the present disclosure, will now be described with reference to the accompanying drawing.

Embodiments are provided so as to thoroughly and fully convey the scope of the present disclosure to the person skilled in the art. Numerous details are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise. The terms "comprises," "comprising," "including," and "having," are open ended transitional phrases and therefore specify the presence of stated features, integers, steps, operations, elements, modules, units and/or components, but do not forbid the presence or addition of one or more other features, integers, steps, operations, elements, components, and/or groups thereof. The particular order of steps disclosed in the method and process of the present disclosure is not to be construed as necessarily requiring their performance as described or illustrated. It is also to be understood that additional or alternative steps may be employed.

The incidence of oral cancer is increasing in India and worldwide. Radiotherapy is used as an adjunct treatment to surgery. Sometimes it can be given as a primary treatment in advanced oral cancer patients where surgery is not possible.

Although, radiotherapy is a necessary line of treatment for cancer, the adverse effects of radiotherapy frequently interfere with continuation of treatment. The adverse effects are due to generation of oxidative stress, inability to control inflammation, reduction in immune response, functional impairment in tissues and improving oral hygiene. These destructive effects result in impairment of quality of life of patients.

Therefore, the present disclosure provides a polyherbal metallo-mineral pharmaceutical kit, for alleviating the adverse effects of radiotherapy.

The present disclosure provides a polyherbal metallo-mineral pharmaceutical kit comprising a first container containing Suvarna Bhasmadi Vati (SBV) in solid dosage form in an amount in the range of 800 mg/day to 1000 mg/day; a second container containing Mouktikyukta Kamdudha Vati (MKV) in solid dosage form in an amount in the range of 800 mg/day to 1200 mg/day; a third container containing Yashtimadhu Ghrut (YTG) in thick, viscous dosage form in an amount in the range of 8 gm/day to 12 gm/day; a fourth container containing Ananta Vati (AV) in solid dosage form in an amount in the range of 0.5 gm/day to 2 gm/day; a fifth container containing Yashtimadhu Taila (YTO) in viscous oily dosage form in an amount in the range of 2 drop/day to 5 drops/day; and a sixth container containing Gandush Churna (GC) in coarse powder dosage form in an amount in the range of 3 gm/day to 10 gm/day.

Suvarna Bhasmadi Vati (SBV) prepared in accordance with the present disclosure provides nourishment to the body, which is hampered due to the conventional anti-cancer therapies. These anti-cancer therapies produce local inflammation, and interfere with the process of absorption of micro nutrients at cellular level. These malfunctions are effectively corrected by SBV.

Mouktikyukta Kamdudha Vati (MKV) alleviates the side effect causing lack of taste and vomiting, by improving digestion. Nausea and loss of taste developed during the course of radiotherapy are well controlled due to its anti-emetic activity.

YTG is prepared in the form of a thick viscous liquid. It minimizes the side effects of radiotherapy by rectifying the disorders of gastro-intestinal system and detoxifies the blood.

Ananta vati has mainly detoxifying effect in the blood. The active components of Ananta Vati have an immediate effect in detoxifying the blood. Ananta Vati provides immediate detoxification of the blood and acts as a free oxidative radical scavenging agent.

The active components of Ananta Vati (AV) and Yashtimadhu Ghrut (YTG), bind together after administration in the body and provide sustained release immunomodulatory effect and exhibit improved anti-oxidant property.

YTO is prepared in the form of a viscous oily liquid.

Prior to use, the Gandush Churna (GC) is prepared into a decoction for gargling, by using water as solvent.

The Gandush Churna is known to exhibit the anti-inflammatory, anti-microbial, antifungal, antioxidant, immuno-modulatory, anti-cancer, chemo-preventive, and radio-protective activities.

The kit of the present disclosure can be used in inflammatory and wound healing conditions and has a synergistic activity.

All the components in the containers containing SBV, MKV, YTG, YTO, GC and AV of the polyherbal metallo-mineral pharmaceutical kit of the present disclosure, when administered together, act synergistically by controlling ROS (Reactive oxygen species) generation, improving anti-inflammatory activity and immunomodulation, and sustaining oral hygiene, thereby reducing the side effects of radiotherapy and improving the quality of life in cancer patients.

In an embodiment, Suvarna Bhasmadi Vati (SBV) is prepared from Suvarna bhasma in an amount ranging from 2 wt % to 7 wt % of the total weight of the Suvarna Bhasmadi Vati (SBV); Mouktik bhasma in an amount ranging from 20 wt % to 35 wt % of the total weight of the Suvarna Bhasmadi Vati (SBV); Guduchi sattva in an amount ranging from 45 wt % to 60 wt % of the total weight of the Suvarna Bhasmadi Vati (SBV); and at least one first excipient in an amount ranging from 5 wt % to 30 wt % of the total weight of the Suvarna Bhasmadi Vati (SBV).

Suvarna bhasma in an amount below 2 wt %, will be sub-therapeutic and in quantities greater than 7 wt %, there will be an overload of the Suvarna Bhasma which will be excreted. Thus, the lower and upper weight percentages of the Suvarna bhasma, Mouktik Bhasma and Guduchi Sattva have been triturated in this composition keeping the above principle in mind.

In an exemplary embodiment, it has been found that for optimum effect, Suvarna Bhasmadi Vati (SBV) should contain 4 wt % Suvarna Bhasma, 26 wt % Mouktik Bhasma, and 53 wt % Guduchi Sattva and a first excipient to the extent of 17 wt %.

In an embodiment, the first excipient is a binder. The binder is selected from the group consisting of gum acacia, guar gum, and xanthan gum.

Suvarna bhasma is also known as incinerated gold and Mouktik bhasma is also known incinerated pearl. Guduchi is the common name for *Tinospora* species. The *Tinospora* (Guduchi) plant is obtained from *Tinospora cordifolia* or *Tinospora sinensis* belonging to the family Menisper-maceae. Particularly the stem of the *Tinospora* (Guduchi) plant is used for making the Sattva.

*Tinospora cordifolia* is indigenous to the tropical areas of India, Myanmar, and Sri Lanka. In the present disclosure, *Tinospora cordifolia* is obtained from Bharatiya Sanskriti Darshan Trust (BSDT), Wagholi, Pune. In the present disclosure, *Tinospora sinensis* is also known as Malabar Gulbel or Gulvel.

*Tinospora sinensis* is found in India, China, Sri Lanka, Nepal, Cambodia, Thailand, Vietnam, and Myanmar. In the present disclosure, *Tinospora sinensis* is obtained from Bharatiya Sanskriti Darshan Trust (BSDT), Wagholi, Pune.

In an embodiment of the present disclosure, Mouktikyukta Kamdudha Vati (MKV) is prepared from, Mouktik bhasma in an amount ranging from 10 wt % to 14 wt % of the total weight of the Mouktikyukta Kamdudha Vati (MKV); Shankha bhasma in an amount ranging from 10 wt % to 14 wt % of the total weight of the Mouktikyukta Kamdudha Vati (MKV); Shouktik bhasma in an amount ranging from 10 wt % to 14 wt % of the total weight of the Mouktikyukta Kamdudha Vati (MKV); Kapardik bhasma in an amount ranging from 10 wt % to 14 wt % of the total weight of the Mouktikyukta Kamdudha Vati (MKV); Praval bhasma in an amount ranging from 10 wt % to 14 wt % of the total weight of the Mouktikyukta Kamdudha Vati (MKV); Guduchi sattva in an amount ranging from 10 wt % to 14 wt % of the total weight of the Mouktikyukta Kamdudha Vati (MKV); Shudhha Gairik in an amount ranging from 10 wt % to 14 wt % of the total weight of the Mouktikyukta Kamdudha Vati (MKV); and at least one second excipient in an amount ranging from 10 wt % to 25 wt % of the total weight of the Mouktikyukta Kamdudha Vati (MKV).

Bhasmas in quantities below 10 wt % of MKV will be sub-therapeutic, and in quantities greater than 14 wt %, there will be an overload of the Bhasma which will be excreted. Thus, the lower and upper weight percentages of Mouktik Bhasma, Praval Bhasma, Shankha Bhasma, Shouktik Bhasma, Kapardik Bhasma, Shudhha Gairik, and Guduchi Sattva have been triturated in this composition keeping the above principle in mind.

In an embodiment of the present disclosure, the second excipient is a binder, selected from the group consisting of gum acacia, guar gum, and xanthan gum.

In an exemplary embodiment, it is found that the optimum effect of Mouktikyukta Kamdudha Vati (MKV) is obtained by using 12 wt % each of Mouktik Bhasma, Praval Bhasma, Shankha Bhasma, Shouktik Bhasma, Kapardik Bhasma, Shudhha Gairik, and Guduchi Sattva with the second excipient comprising natural gum such as gum acacia in an amount of 16 wt %.

The Praval (coral) has a rejuvenating effect, anti-pyretic effect, and detoxifying effect, and it can boost immunity, which is beneficial in radiotherapy induced adverse effects like stomatitis and loss of taste. Trituration of Praval in rose water (Praval Pishti) gives additional cooling effect.

The ingredients Mouktik Bhasma, Praval Bhasma, Shankha Bhasma, Shouktik Bhasma, Kapardik Bhasma, Shudhha Gairik and Guduchi Sattva are blended together to form powder. At least one second excipient is added to the powder blend to form a dough using purified water. Pellets are formed from this dough having average weight of 5 gm each. The pellets are tray-dried typically at temperature in the range of 40° C. to 45° C. The dried pellets are granulated in a mixer grinder and the dry granules are taken for compression tableting. The average weight of each uncoated tablet is 300 mg±5%. The typical shelf life of the tablets is 3 years. The solid dosage form can be in a form selected from the group consisting of tablet, pill, and capsule.

The third container containing Yashtimadhu Ghrut (YTG) is an aqueous or alcoholic extract obtained from the stems and stolons of Yashtimadhu, wherein the extract is in an amount ranging from 2 wt % to 10 wt % of the total weight of the Yashtimadhu Ghrut (YTG); and Ghee is in an amount ranging from 95 wt % to 98 wt % of the total weight of the Yashtimadhu Ghrut (YTG).

The extract of Yashtimadhu is a decoction obtained by using at least one solvent selected from the group consisting of alcohol, water and a mixture thereof. Alternatively, the extract is obtained by supercritical extraction;

YTG helps in reducing local inflammation and inflammation in the gastrointestinal (GI) tract. It improves gross as well as micro level absorption of the actives, thus improving metabolism.

The ghee obtained from Cow's milk has independent medicinal properties. It improves appetite, increases strength, eliminates toxins and excessive heat, and heals ulcers. All these properties of ghee reduce adverse effects of radiotherapy. Additionally, cow's ghee in YTG acts as a binder and improves the mode of action synergistically.

In one embodiment, the aqueous decoction of stems/ stolons of Yashtimadhu is mixed with cow's ghee. The mixture is heated uniformly with stirring to evaporate the water completely. The complete removal of water is confirmed by the wick test. The active ingredients of the decoction are dissolved or dispersed in the hot ghee. The hot mixture so obtained is filtered through muslin cloth to obtain YTG. YTG can be administered at a dose of 8 gm to 12 gm per day by oral administration and can also be used for local application in the oral cavity. The shelf life of YTG is 2 years.

The biological name of Yashtimadhu is *Glycyrrhiza glabra* belonging to family family Fabaceae. It is commonly known as Liquorice.

*Glycyrrhiza glabra* holds a subcosmopolitan distribution in Asia, Australia, Europe, and the Americas while it is largely cultivated in these areas. In the present disclosure, *Glycyrrhiza glabra* is obtained from Bharatiya Sanskriti Darshana Trust, Wagholi, Pune.

Cow's Ghee in the present disclosure is obtained from Bharatiya Sanskriti Darshan Trust (BSDT), Wagholi, Pune.

In an embodiment, Ananta Vati (AV) is prepared from a powder obtained from dried roots of Ananta in an amount ranging from 75 wt % to 92 wt % of the total weight of Ananta Vati (AV) and at least one, third excipient in an amount ranging from 8 wt % to 25 wt % of the total weight of Ananta Vati (AV). Ananta or *Decalepis hamiltonii* is a species of plant in the family Apocynaceae. It is endemic to Peninsular India. In the present disclosure, *Decalepis hamiltonii* was obtained from Bharatiya Sanskriti Darshan Trust (BSDT), Wagholi, Pune.

In an embodiment, the powder form of dried roots of Ananta has a particle size ranging from 150 to 180 microns.

The fifth container containing Yashtimadhu Taila (YTO) is an aqueous or alcoholic extract obtained from the stems and stolons of Yashtimadhu, wherein said extract is in amount ranging from 2 wt % to 10 wt % of the total weight of Yashtimadhu Taila (YTO); and sesame oil is in an amount ranging from 95 wt % to 98 wt % of the total weight of the Yashtimadhu Taila (YTO).

YTO in its unique combination for nasal application, assists in minimizing the side effects like trismus, xerostomia by imparting soothing effect and softening of the oral muscles. Sesame oil present in YTO provides the synergistic smoothening effect.

The extract of Yashtimadhu is a decoction obtained by using at least one solvent selected from the group consisting of alcohol, water and a mixture thereof. Alternatively, the extract is obtained by supercritical extraction.

Aqueous decoction of stems/stolons of Yashtimadhu is mixed with sesame oil. The mixture is heated uniformly with stirring to evaporate the water completely. The complete removal of water is confirmed by the wick test. The active ingredients of the decoction are dissolved or dispersed in the hot sesame oil. The hot mixture so obtained is filtered through muslin cloth to obtain YTO. The shelf life of YTO is 3 years.

The botanical name of Yashtimadhu is *Glycyrrhiza glabra* belonging to family family Fabaceae. It is commonly known as Liquorice.

*Glycyrrhiza glabra* has a subcosmopolitan distribution in Asia, Australia, Europe, and America, and it is largely cultivated in these areas.

In the present disclosure, *Glycyrrhiza glabra* is obtained from Bharatiya Sanskriti Darshan Trust, Wagholi, Pune.

In an embodiment, Gandush Churna (GC) is prepared from a coarse powder of pericarp of Haritaki in an amount ranging from 23 wt % to 34 wt % of the total weight of the Gandush Churna (GC); a coarse powder of pericarp of Bibhitaki in an amount ranging from 23 wt % to 34 wt % of the total weight of Gandush Churna (GC); a coarse powder of pericarp of Amalaki in an amount ranging from 23 wt % to 34 wt % of the total weight of Gandush Churna (GC); and a coarse powder of rhizome of Haridra in an amount ranging from 11 wt % to 17 wt % of the total weight of Gandush Churna (GC).

In one embodiment, Gandush Churna (GC) is prepared from coarse powders of, pericarp of *Terminalia chebula* (Haritaki) in an amount ranging from 23 wt % to 34 wt % of the total weight of the Gandush Churna (GC); pericarp of *Terminalia bellerica* (Bibhitaki) in an amount ranging from 23 wt % to 34 wt % of the total weight of Gandush Churna (GC); pericarp of *Phyllanthus emblica* (Amalaki) in an amount ranging from 23 wt % to 34 wt % of the total weight of Gandush Churna (GC); and dried rhizome of *Curcuma longa* (Haridra) in an amount ranging from 11 wt % to 17 wt % of the total weight of Gandush Churna (GC).

In one embodiment, the whole dried pericarp and dried rhizomes are pulverized separately and passed through sieves to get evenly distributed particles ranging from 355 to 425 microns. The coarse powders of Haritaki, Bibhitaki, Amalaki and Haridra are mixed in a ratio of 1:1:1:0.5 to obtain a homogenous coarse powdered Gandush churna. The typical shelf life of this coarse powder is 2 years.

In another embodiment, the Gandush Churna (GC) is prepared into a decoction mixing 6 gm of the GC powder with 385 ml water, which is reduced to 192 ml by boiling.

In yet another embodiment, the Gandush Churna (GC) is prepared into a decoction by soaking Gandush Churna (GC) in 64 times of water for boiling and is reduced to half for gargle therapy.

*Terminalia chebula* (Gaertn.) Retz. is know as Haritaki belonging to the family Combretaceae. The plant is found throughout India, chiefly in deciduous forests. It occurs abundantly in North India. Its range extends southwards at 300 to 900 m altitude. In the present disclosure, *Terminalia chebula* was obtained from Bharatiya Sanskriti Darshan Trust (BSDT), Wagholi, Pune.

*Terminalia bellirica* (Gaertn.) Roxb. (syn. *T. punetata* Roxb., *Myrobalamus belerica* B. Gaertn.) is know as Bibhitaki and belongs to the family Combretaceae. The plant is common throughout India in plains and lower hills, chiefly in deciduous forests, at 900 m elevation where the climate is not very dry. It is also found in forests of Burma and Sri Lanka. In the present disclosure, *Terminalia bellerica* was obtained from Bharatiya Sanskriti Darshan Trust (BSDT), Wagholi, Pune.

*Phyllanthus emblica* is known as Amalaki and belongs to family Phyllanthaceae/Euphorbiaceae. It is a deciduous tree found throughout India chiefly in deciduous forests or is widely cultivated. In the present disclosure, *Phyllanthus emblica* was obtained from Bharatiya Sanskriti Darshan Trust (BSDT), Wagholi, Pune.

*Curcuma longa* is known as Haridra (Turmeric). It is a flowering plant, of the ginger family, Zingiberaceae. The plant is a perennial, rhizomatous, herbaceous native to the Indian subcontinent and Southeast Asia, that requires temperatures between 20 and 30° C. and a considerable amount The polyherbal metallo-mineral pharmaceutical kit reduces oxidative stress, and improves the immune response in patients treated with radiotherapy for improving the quality of life in patients The kit disclosed in present disclosure comprises solid dosage forms selected from the group consisting of tablet, pill, and capsule.

The first excipient, second excipient and third excipient are independently selected from the group consisting of gum acacia, guar gum, and xanthan gum.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure is further described in light of the following experiments which are set forth for illustration purpose only and not to be construed for limiting the scope of the disclosure. The following experiments can be scaled *up to industrial/commercial scale and the results obtained can be extrapolated to industrial scale.

EXPERIMENTAL DETAILS

Experiment 1: Components of the Kit of the Present Disclosure

A polyherbal metallo-mineral pharmaceutical kit prepared in accordance with the present disclosure.

Example 1: Polyherbal Metallo-Mineral Pharmaceutical Kit

Table 1 below shows the dosage range of the polyherbal metallo-mineral pharmaceutical kit administered per day.

TABLE 1

| | Daily dosage range of the Polyherbal metallo-mineral pharmaceutical kit | | |
|---|---|---|---|
| Sr. No. | Content of containers of kit | Dosage range recommended per day | Dosage per day administered in Example 1 |
| 1 | Suvarna Bhasmadi Vati (SBV) | 800 mg—1000 mg for oral administration | 2 tablets of 237 mg for oral administration twice a day |
| 2 | Mouktikyukta Kamdudha Vati (MKV) | 400 mg-600 mg for oral administration | 2 tablets of 300 mg for oral administration |
| 3 | Yashtimadhu Ghrut (YTG) | 8 gm—12 gm for oral administration 2 drops for local application | 5 gm (1 tsp) for oral administration twice a day 2 drops for local application |
| 4 | Ananta Vati (AV) | 0.5 gm—2 gm for oral administration | 1.2 gm (4 tablets of 300 mg) for oral administration |
| 5 | Yashtimadhu Taila (YTO) | 1-5 drops for nasal application | 2 drops (each nostril) for nasal application |
| 6 | Gandush Churna (GC) | 3-10 gm powder for preparing gargling decoction | 6 gm—decoction made with 385 ml water, reduced to 192 ml by boiling, for gargling | of annual rainfall to thrive. In the present disclosure, *Curcuma longa* was obtained from Bharatiya Sanskriti Darshan Trust (BSDT), Wagholi, Pune.

The kit envisaged in the present disclosure is suitable as an adjuvant in the treatment for oral cancer in alleviating adverse side effects of radiotherapy and improving the quality of life of patients.

Example 2: Composition of Suvarna Bhasmadi Vati (SBV)

SBV was prepared by varying the amount of each of its components, as given below in Table 2. Batch-1 showed the best results on administration.

TABLE 2

| | | | Quantity for 5 kg batch— | Quantity for 5 kg batch— | Quantity for 5 kg batch— |
|---|---|---|---|---|---|
| Sr. No. | Contents | Latin name/ English Name | Batch 1 | Batch 2 | Batch 3 |
| 1 | Suvarna Bhasma | Incinerated Gold | 210.97 g | 110 g | 350 g |
| 2 | Mouktik Bhasma | Incinerated Pearl | 1318.56 g | 1700 g | 1000 g |
| 3 | Aqueous extract of *Tinospora cordifolia*/sinensis (Guduchi Sattva) | Starch of *Tinospora cordifolia*/ sinensis | 2637.1 g | 2940 g | 2250 g |
| 4 | Gum *Acacia* powder | . . . | 833.33 g | 250 g | 1400 g |

Process for Preparing Suvarna Bhasmadi Vati (SBV) in Accordance with Table 2

Step 1: Preparation of Suvarna Bhasma

Initially, 300 gm of Suvarna foils were amalgamated with 2500 gm of metallic mercury and 2500 gm of sulphur powder having particle size 150 microns and then incinerated 18 times each at 650° C. for 6 hours to get incinerated Suvarna. For stabilization, the incinerated Suvarna was triturated for 6 hours with 200 ml fresh juice of the leaves of *Ocimum sanctum* (Tulsi) and further incinerated at 600° C. for 5 hours. This process of incineration in Tulsi juice was repeated 25 times to obtain Suvarna Bhasma having particle size in the range of 20-500 nm (average particle size 350 nm). The particle size of the so obtained Suvarna Bhasma were analysed by particle size analyser (90 plus from Brookhaven Instruments, USA).

Tulsi—*Ocimum sanctum* is also known as holy basil of the family Lamiaceae. *Ocimum sanctum* was obtained from Bharatiya Sanskriti Darshan Trust (BSDT), Wagholi, Pune.

Specification of Suvarna Bhasma:

Description: Brown coloured, very fine free flowing powder

Loss on Drying—NMT 0.5% w/w

Loss on Ignition—NMT 1% w/w

Acid insoluble ash—90 to 98% w/w

Assay as Au—NLT 85% w/w

Step 2: Preparation of Mouktik Bhasma

8 Kg Mouktik (pearl) was boiled in 32 L of butter milk having curd to water ratio of 1:2 w/v and pH of 3, to obtain purified Mouktik. The so obtained purified Mouktik was powdered and triturated with 4 L of rose water to obtain triturated powder. The triturated powder was then incinerated using cow-dung cakes at 700° C. to obtain Mouktik Bhasma (incinerated pearl).

Specification of Mouktik Bhasma:

Description: Greyish white coloured, very fine powder

Loss on Drying—NMT 0.5% w/w

Acid insoluble ash—NMT 2% w/w

Calcium assay—38 to 40% w/w pH—10 to 11

Step 3: Preparation of Guduchi Sattva (Extraction of Starch from *Tinospora cordifolia*)

50 Kg of fresh stems of *Tinospora cordifolia* were chopped into small pieces. These pieces were crushed and then soaked for 12 hours in 4 times (w/v) of potable water (200 L) in a stainless steel vessel. The mixture was macerated in water thoroughly and filtered slowly to obtain solution containing aqueous extract of *Tinospora cordifolia*. The solution thus obtained was kept aside for 12 hours to obtain supernatant and smooth starchy sediment of *Tinospora cordifolia*. The supernatant was carefully separated to obtain smooth starchy sediment. The smooth starchy sediment of *Tinospora cordifolia* was evaporated in an oven at 45° C. to obtain Guduchi Sattva in the form of dry starch.

Specification of Guduchi Sattva (Starch Extract of *Tinospora cordifolia*):

Description: Greyish white coloured very fine free flowing starchy powder

Loss on Drying—NMT 5% w/w

Acid insoluble ash—NMT 1% w/w

Gelation temperature—60 to 75° C.

Step 4: Preparation of SBV

In a mixer, Suvarna bhasma, Mauktik bhasma, Guduchi Sattva (starch from *Tinospora cordifolia*), and gum acacia were mixed in a proportion given in Table 2. To this mixture, sufficient amount of water was added to obtain a dough. The dough was further pelletized to obtain pellets. The pellets were dried in oven at 45° C. to obtain dried pellets. The dried pellets were grinded to obtain granules having powder to granule ratio of 30:70. The mixture of granules and powder was compressed in tablet punching machine to obtain compressed tablet of weight 237±5 mg.

Specification of SBV:

Appearance: Grey colour, round

Shape: Biconvex tablets

Weight variation: 0.2210 to 0.2300

Average weight: 0.2300 to 0.2500

Hardness: 1-2 Kg/cm$^2$

Friability: NMT 1% w/w

Disintegration Time: NMT 30 min

Diameter: 7 to 7.5 mm

Width: 3.3 to 4.6 mm

Acute toxicity: LD 50 >2000 mg/kg

Example 3: Composition of Mouktikyukta Kamdudha Vati (MKV)

MKV was prepared using the following ingredients as given in Table 3. Batch-1 showed the best results on administration

TABLE 3

| | | | Quantity for 30 kg batch— | Quantity for 30 kg batch— | Quantity for 30 kg batch— |
|---|---|---|---|---|---|
| Sr. No. | Contents | Latin name/English Name | Batch 1 | Batch 2 | Batch 3 |
| | | *Mouktikyukta Kamdudha Vati (MKV)* | | | |
| 1 | Mouktik Bhasma | Incinerated Pearl | 3572 g | 3500 | 4000 |
| 2 | Shankha Bhasma | Incinerated Conch | 3572 g | 3000 | 3800 |
| 3 | Shouktik Bhasma | Incinerated Pearl Shell | 3572 g | 3000 | 3800 |
| 4 | Kapardik Bhasma | Incinerated Cowrie | 3572 g | 3000 | 3800 |
| 5 | Praval Bhasma | Incinerated Coral | 3572 g | 3500 | 3800 |
| 6 | An aqueous extract of *Tinospora cordifolia*/sinensis | Starch of *Tinospora cordifolial* sinensis | 3572 g | 3500 | 4000 |
| 7 | Shudhha Gairik | Red ochre roasted in cow ghee | 3572 g | 3000 | 3800 |
| 8 | Gum *Acacia* powder | . . . | 5000 g | 7500 | 3000 |

Process for Preparing Mouktikyukta Kamdudha Vati (MKV) in Accordance with Table 3

Mouktik bhasma, Shankha bhasma, Shouktik bhasma, Kapardik bhasma, Praval bhasma (all these five bhasma were prepared using conventional textual methods), starch of *Tinospora cordifolia/sinensis*, Shudhha Gairik and gum acacia powder were mixed in the proportion given in Table 3. To this mixture, sufficient amount of potable water was added to obtain a dough. The dough was further pelletized to obtain pellets. The pellets were dried in oven at 45° C. to obtain dried pellets. The dried pellets were grinded to obtain granules having powder to granule ratio of 30:70. The mixture of granules and powder was compressed in tablet punching machine to obtain compressed tablet of weight 300±5 mg.

Specification of Shankha Bhasma:
   Description—Greyish white very fine powder
   Loss on drying—NMT 1% w/w
   Acid insoluble ash—NMT 2% w/w
   pH—9 to 10
   Calcium assay as Ca—38 to 40% w/w
Specification of Shouktik Bhasma:
   Description—Greyish white very fine powder
   Loss on drying—NMT 1% w/w
   Acid insoluble ash—NMT 2% w/w
   pH—10 to 11
   Calcium assay as Ca—38 to 40% w/
Specification of Kapardik Bhasma:
   Description—Greyish white very fine powder
   Loss on drying—NMT 1% w/w
   Acid insoluble ash—NMT 2% w/w
   pH—10 to 11
   Calcium assay as Ca—38 to 40% w/w
Specification of Praval Bhasma:
   Description—Greyish white very fine powder
   Loss on drying—NMT 1% w/w
   Acid insoluble ash—NMT 2% w/w
   pH—10 to 11
   Calcium assay as Ca—40 to 45% w/w
Specification of Mouktik (Pearl) Bhasma:
   Description—Greyish white very fine powder
   Loss on drying—NMT 1% w/w
   Acid insoluble ash—NMT 2% w/w
   pH—10 to 11
   Calcium assay as Ca—38 to 40% w/w
Specification of Shudhha Gairik (Red Ochre):
   Loss on drying—NMT 1% w/w
   Iron assay—NLT 15% w/w Silica assay—18 to 20% w/w
Oil content—3 to 3.5% w/w
Specification of Guduchi Sattva (Starch of *Tinospora cordifolia/sinensis*):
   Loss on drying—4 to 5% w/w
   Acid Insoluble ash—NMT 1% w/w
   Gelation temperature—60 to 75° C.
Specification of MKV:
   Description: Light brown colour
   Shape: Round biconvex tablet
   Weight variation: 0.2850 to 0.3150
   Average weight: 0.2900 to 0.3100
   Hardness: 2 to 4 Kg/cm$^2$
   Friability: NMT 1% w/w
   Disintegration Time: NMT 30 min
   Diameter: 7 to 8 mm
   Width: 3 to 4 mm
   Acute Toxicity: LD 50 >2000 mg/kg Example 4: Composition of Yashtimadhu Ghrut (YTG)

YTG was prepared by varying the amount of each of its components, as given below in Table 4. Batch-1 showed the best results on administration.

TABLE 4

| | | | Quantity for 10 kg batch of finished product | Quantity for 10 kg batch of finished product | Quantity for 10 kg batch of finished product |
|---|---|---|---|---|---|
| Sr. No. | Contents | Common Name | Batch 1 | Batch 2 | Batch 3 |
| | | *Yashtimadhu Ghrut (YTG)* | | | |
| 1 | Decoction of *Glycyrrhiza glabra* | Yashtimadhu | 10000 ml | 7500 ml | 12500 ml |
| 2 | Clarified butter | Ghrut, Ghrita, Cow's ghee | 10000 g | 10000 g | 10000 g |

Process for Preparing Yashtimadhu Ghrut (YTG) in Accordance with Table 4

2500 gm of dried stems/stolons of *Glycyrrhiza glabra* was obtained and pulverised into coarse powder. The coarse powder of *Glycyrrhiza glabra* was separately processed in 40 L of water to prepare 10 L decoction, wherein the ratio of *Glycyrrhiza glabra* stems/stolons to water was 1:16 and reduced to ¼$^{th}$ to obtain the decoction of *Glycyrrhiza*

*glabra*. The decoction and 10 Kg clarified butter were mixed in a proportion 1:1 (v/w). The so obtained mixture was heated uniformly at 100° C. for 6 hrs to evaporate water completely to obtain 10 kg of the YTG composition of the present disclosure.

Specification of YTG:

Description: Yellow coloured sticky thick ghee (semi-solid) having characteristic odour Specific gravity at 25° C.: 0.9010-0.9130

Refractive index at 25° C.: 1.535-1.538

Acid value: 1.1-1.6

Saponification value: 200-260

Unsaponifiable matter: 0.3-3.5

Iodine value: 20-40

Peroxide value: 0.5-2

Congealing point: 26-30

Moisture content: Not more than 0.5%

RM value: 20-40

Microbial limits: Total Viable Count (TVC)—NMT 105/gm

: Coliform—Absent

: Fungal count—Absent

Heavy metal limits: Not more than 20 ppm

Thin Layer Chromatography Toluene:Ethyl acetate:Formic acid: 5:4:1

UV 254—05 spots Rf: 0.63, 0.70 (Both Blue), 0.72 (Green), 0.75, 0.95 (Both blue)

UV 365 nm—07 spots Rf: 0.56, 0.62 (Flu. Blue), 0.65 (Green), 0.70 (Yellow), 0.72 (Red), 0.75, 0.80 (Both Flu. Blue)

Anisaldehyde Sulphuric acid reagent 11 spots Rf: 0.55 (Blue) 0.57 (Violet), 0.65 (Pink Violet), 0.67 (Red) 0.70 (Blue), 0.72 (Yellow), 0.73 (Violet), 0.86, 0.80 (Both Blue), 0.92 (Green), 0.95 (Blue)

Example 5: Composition of Ananta Vati (AV)

AV was prepared by varying the amount of each of its components, as given below in Table 5. Batch-1 showed the best results on administration.

TABLE 5

| | | | Ananta Vati | | |
|---|---|---|---|---|---|
| Sr. No. | Contents | Common Name | Quantity for 30 kg batch— Batch 1 | Quantity for 30 kg batch— Batch 2 | Quantity for 30 kg batch— Batch 3 |
| 1 | Powder of *Decalepis hamiltonii* | Ananta | 25000 g | 22500 | 27500 |
| 2 | Gum *Acacia* powder | . . . | 5000 g | 7500 | 2500 |

Process for Preparing Ananta Vati in Accordance with Table 5

In a mass mixer, powders of *Decalepis hamiltonii* and gum acacia were mixed in a proportion given in Table 5. To this mixture, sufficient amount of potable water was added to obtain a dough. The dough was further pelletized to obtain pellets. The pellets were dried in oven at 45° C. to obtain dried pellets. The dried pellets were grinded to obtain granules having powder to granule ratio of 30:70. The granules and powder were compressed in tablet punching machine to obtain compressed tablet of weight 300±5 mg.

Specification of Ananta Vati:

Description: Light brown colour

Shape: Round biconvex tablets

Weight variation: 0.2850 to 0.3150

Average weight: 0.2900 to 0.3100

Hardness: 1 to 4 Kg/cm$^2$

Friability: NMT 1% w/w

Disintegration Time: NMT 15 min

Diameter: 10 to 11 mm

Width: 4 to 5 mm

Example 6: Composition of YTO

YTO was prepared by varying the amount of each of its components, as given below in Table 6. Batch-1 showed the best results on administration.

TABLE 6

| | | | Ingredients for preparing YTO | | |
|---|---|---|---|---|---|
| Sr. No. | Contents | Common Name | Quantity for 1 L batch of finished product Batch 1 | Quantity for 1 L batch of finished product Batch 2 | Quantity for 1 L batch of finished product Batch 3 |
| 1 | Decoction of *Glycyrrhiza glabra* | Yashtimadhu | 1000 ml | 750 ml | 1250 ml |
| 2 | Sesame Oil | | 1000 ml | 1000 ml | 1000 ml |

Process for Preparing YTO in Accordance with Table 6

250 gm of dried stems/stolons of *Glycyrrhiza glabra* was obtained and pulverised into coarse powder. The coarse powder of *Glycyrrhiza glabra* was separately processed in 4 L of water to prepare 1000 ml decoction, wherein the ratio of *Glycyrrhiza glabra* stems/stolons to water was 1:16 and reduced to ¼$^{th}$ to obtain the decoction of *Glycyrrhiza glabra*. The decoction and 1000 ml sesame oil were mixed in a proportion 1:1 (v/v). The so obtained mixture was heated uniformly at 100° C. for 60 min to evaporate water completely to obtain 1000 ml of the YTO composition of the present disclosure.

Specification of YTO:

Description: Yellow coloured thick viscous oil (liquid) with characteristic odour.

Specific gravity at 25° C.: 0.9100-0.9180

Refractive index at 25° C.: 1.5450-1.5500

Acid value: 1.00-3.500

Saponification value: 170-260

Unsaponifiable matter: 0.5-2

Iodine value: 30-120

Peroxide value: 0.5-4

Weight per ml at 25° C.: 0.9070-0.9170

Moisture content: Not more than 0.5%

Cotton seed oil presence: Absent

Microbial limits: Total Viable Count (TVC)—NMT 105/ gm
: Fungal count—103/gm
Heavy metal limits: Not more than 20 ppm
Thin Layer Chromatography Toluene:Ethyl acetate:Formic acid: 5:4:1
UV 254 nm—4 spots: Rf—0.14, 0.35, 0.56 (All blue)
UV 365 nm—1 spot Rf: 0.30 (Light Blue)
Liberman Burchard Reagent—5 spots Rf: 0.30 (Brown), 0.35 (Violet), 0.50 (Pink), 0.80 (Grey), 0.98 (Yellow)

Example 7: Composition of Gandush Churna (GC)

GC was prepared by varying the amount of each of its components, as given below in Table 7. Batch-1 showed the best results on administration.

TABLE 7

Ingredients for preparing Gandush Churna

| Sr. No. | Contents | Common Name | Quantity for 10 kg batch Batch 1 | Quantity for 10 kg batch Batch 2 | Quantity for 10 kg batch Batch 3 |
|---|---|---|---|---|---|
| 1 | Coarse powder of *Terminalia chebula* | Haritaki | 2.86 kg | 2.43 kg | 3.29 kg |
| 2 | Coarse powder of *Terminalia bellerica* | Bibhitaki | 2.86 kg | 2.43 kg | 3.29 kg |
| 3 | Coarse powder of *Phyllanthus emblica* | Amalaki | 2.86 kg | 2.43 kg | 3.29 kg |
| 4 | Coarse powder of *Curcuma longa* | Haridra | 1.42 kg | 2.7 kg | 0.13 kg |

Process for Preparing Gandush Churna (GC) in Accordance with Table 7

In a pulveriser, whole dried pericarps of Haritaki, Bibhitaki and Amalaki while dried rhizomes of Haridra were pulverized separately and passed through sieves to get evenly distributed particles ranging from 355 to 425 microns, each. These coarse powders of Haritaki, Bibhitaki, Amalaki and Haridra were mixed in a mass mixer (as given in Table 7) maintaining a ratio of 1:1:1:0.5 (w/w) to obtain a homogenous coarse powder of Gandush churna.
Specification of Gandush Churna:
Description: Coarse mixture of particles, greenish, brown, orange and black
Moisture content: Not more than 10%
Total Ash value: 3-4.5% w/w
Acid insoluble ash: NMT 1% w/w
Water soluble extractive: 30-50% w/w
Alcohol soluble extractive: 18-28% w/w
Bulk density: 0.5500-0.6500 gm/cc
Microbial limits: Total Viable Count (TVC)—NMT 105/ gm : Yeast and Mould—NMT 103/gm
: *E. coli*—Absent
Thin Layer Chromatography: Toluene:Ethyl acetate: 9:1
Visible—3 spots Rf: 0.05, 0.10, 0.20 (All Yellow)
366 nm—3 spots 0.05 (Yellow), 0.12 (Flu. Lemon yellow), 0.20 (Flu. Yellow)
Anisaldehyde sulphuric acid—2 spots Rf: 0.10, 0.20 (Blue)
In one embodiment, Gandush Churna (GC) was prepared into a decoction for gargling.
Process for Preparing a Decoction of Gandush Churna (GC)
A decoction of Gandush Churna (GC) was prepared by soaking Gandush Churna (GC) of Table 7 in 64 times water, to obtain a mixture. The mixture was then boiled until about 50% of the water was lost. The decoction so obtained was used for gargle therapy.

Experiment 2: Efficacy Study of the Decoction of Gandush Churna (GC) as a Gargle Therapy Oral cavity cancer patients (n=6) on radiotherapy were enrolled for the present study. Total microbial count and identification of microbiota in the oral cavity as well as radiation induced side effects, graded as per Common Terminology Criteria for Adverse Events (version 4.3), were noted before and after the treatment was carried out. Change in oral microbial load and shift in symptom gradations were then analysed.

Inclusion-Exclusion criteria: Patients diagnosed with oral cancers, irrespective of stage and grade, between age 16-65 years, completed radiotherapy before enrolment, having active oral mucosal inflammation of grade 2-3, infection, local pain, xerostomia, trismus, dysphagia etc., and having oral pathological microbial load by oral swab test, were included in the study.

Patients medically compromised; having active addictions like tobacco chewing, smoking, alcohol; and receiving other gargle or local therapy, local and/or systemic anti-inflammatory, antibiotic and anti-fungal drugs were excluded from the study.

Intervention: Patient was clinically assessed for local symptoms viz. oral mucositis/stomatitis, pain, trismus, dysgeusia, dysphagia and xerostomia and graded. Total 160 ml of decoction, with 30-40 mL aliquots, holding for 30 s each, was used for gargles twice a day, for 7 days.

Outcomes: Patient was clinically examined after 7 days. Oral swab was taken (Day 0 and 8) with sterile swab stick and cultured for bacteria, yeast and fungal load while growth was observed after 24-48 h. They were identified with automated VITEK 2 (Biomerieux, USA) compact identification and Antibiotic Susceptibility Testing system. Antimicrobial potential of the gargles was expressed as total viable count (CFU/mL). Two patients were treated for additional 2-3 weeks and assessed.

TABLE 8

Clinical study of decoction of Gandush Churna (GC) as a gargling therapy in oral cavity cancer patients undergone radiotherapy

| Sr. No. | Patient Code | Age (Y)/ Sex | Diagnosis | Day | Dysphagia | Xerostomia | Local Pain | Stomatitis | Excessive salivation | Trismus | Dysgeusia |
|---|---|---|---|---|---|---|---|---|---|---|---|
| 1 | PPM | 45/Male | CA | 0 | 2 | 0 | 2 | 0 | 0 | 0 | 1 |
| | | | Hypopharynx | 8 | 1 | 0 | 1 | 0 | 0 | 0 | 1 |

TABLE 8-continued

Clinical study of decoction of Gandush Churna (GC) as a gargling
therapy in oral cavity cancer patients undergone radiotherapy

| Sr. No. | Patient Code | Age (Y)/ Sex | Diagnosis | Day | Dysphagia | Xerostomia | Local Pain | Stomatitis | Excessive salivation | Trismus | Dysgeusia |
|---|---|---|---|---|---|---|---|---|---|---|---|
| | | | with cervical node metastasis | | | | | | | | |
| 2 | DVL | 45/Male | CA Right | 0 | 1 | 2 | 2 | 2 | 0 | 3 | 1 |
| | | | Gingivobuccal mucosa | 8 | 0 | 1 | 1 | 0 | 0 | 3 | 1 |
| 3 | DRB | 45/Male | CA Right | 0 | 0 | 0 | 2 | 2 | 0 | 1 | 0 |
| | | | Buccal mucosa | 8 | 0 | 0 | 0 | 1 | 0 | 1 | 0 |
| 4 | MMP | 44/Male | CA Left buccal | 0 | 0 | 0 | 3 | 3 | 0 | 2 | 1 |
| | | | mucosa with recurrence | 8 | 0 | 0 | 1 | 1 | 0 | 2 | 1 |
| 5 | NSM | 64/Male | CA Left buccal | 0 | 0 | 0 | 2 | 2 | 0 | 2 | 0 |
| | | | mucosa | 8 | 0 | 0 | 2 | 1 | 0 | 2 | 0 |
| 6 | RLB | 48/Male | CA Tongue | 0 | 3 | 0 | 2 | 2 | 0 | 2 | 1 |
| | | | with | 8 | 3 | 0 | 1 | 2 | 0 | 2 | 1 |
| | | | recurrence | 15 | 3 | 0 | 1 | 2 | 0 | 2 | 1 |

TABLE 9

Oral microbial load of oral cavity cancer patients
treated with decoction of Gandush Churna (GC)

| Sr. No | Patient code | Day | Total viable count (CFU/mL) | Gram stain | Organism isolated | Fungal growth |
|---|---|---|---|---|---|---|
| 1 | PPM | 0 | >$10^5$ | Gram negative rods seen | *E. coli* | No growth |
| | | 7 | No growth | — | — | No growth |
| | | 14 | No growth | — | — | No growth |
| | | 21 | No growth | — | — | No growth |
| 2 | DVL | 0 | >$10^5$ | Gram negative rods seen | *E. coli* | *Candida* spp <$10^3$ |
| | | 7 | No growth | — | — | *Candida* spp <$10^3$ |
| 3 | DRB | 0 | No growth | — | — | *Candida* spp <$10^2$ |
| | | 7 | No growth | — | — | *Candida* spp <10 |
| 4 | MMP | 0 | No growth | — | — | *Candida* spp <$10^2$ |
| | | 7 | No growth | — | — | *Candida* spp <10 |
| 5 | NSM | 0 | <$10^2$ | Gram positive cocci in cluster | *S. aureus* | *Candida* spp <$10^2$ |
| | | 7 | No growth | — | — | *Candida* spp <$10^2$ |
| 6 | RLB | 0 | >$10^5$ | Gram negative rods seen | *P. aeruginosa* | *Candida* spp >$10^5$ |
| | | 7 | >$10^5$ | Gram positive rods seen | *S. aureus* | *Candida* spp >$10^2$ |
| | | 14 | No growth | — | — | No growth |

Result: All the patients exhibited for local pain (grade 2); 83.33% showed oral mucositis/stomatitis (grade 2-3) and trismus (grade 2-3) while 66.67, 50 and 33.33% patients complained dysgeusia (grade 1), dysphagia (grade 2) and xerostomia (grade 2), respectively, before gargling. Pathogenic bacterial viz., *E. coli, S. aureus, P. aeruginosa*) and/or fungal viz., *Candida* spp., strains were positive in the oral cavity swabs of all the patients. There was a significant improvement in gradation score of symptoms like local pain (p=0.01) and stomatitis (p=0.04) after 7 days of gargles.

The gradation of symptoms dysphagia and xerostomia showed considerable decrease, but trismus and dysgeusia did not show any change as illustrated in Table 8. Gargle decoction exhibited significant antibacterial activity against *E. coli, S. aureus* and *P. aeruginosa* while mild anti-fungal activity against *Candida* spp upon 7 days gargles. One patient required 14 days gargle for whole antibacterial and antifungal result. Moreover, in one patient with no growth on 8th day, continuous gargle for additional 14 days also displayed no growth of microbes as depicted in Table 9.

Experiment 3: Efficacy Studies of the Kit of the
Present Disclosure

Various types of studies were conducted to evaluate the efficacy of the kit of the present disclosure. In all these studies, 175 oral cancer patients scheduled for radiotherapy were included. Out of these, 115 patients (Group 1—Study group), were given additional polyherbal metallo-mineral pharmaceutical kit of the present disclosure, whereas the remaining 60 patients (Group 2—Control group) were not provided with any additional polyherbal metallo-mineral pharmaceutical kit of the present disclosure. The stage and grade of the disease were matched for both Group 1 and Group 2. Pharmaceutical compositions of the kit were given from the start of radiotherapy till the completion of radiotherapy.

Inclusion Criteria

Oral cavity cancer patients of all stages and grades, scheduled for radiotherapy dose up to 7000 Cgy in 30-35 fractions for 6-7 weeks.

Exclusion Criteria

Patients taking other Ayurvedic drugs for cancer or any other ailment and patients with oral cavity cancer scheduled for palliative radiotherapy.

Outcome Measures—

Time points for assessment of outcome measures—

A—Before radiotherapy

B—Mid radiotherapy

C—End of radiotherapy

A. Clinical Investigations

The patients were followed-up for:

a. Clinical assessment of adverse effects and its grading using CTCAE 4.03 Version. Stomatitis, dysphagia and nausea recorded on the scale of grade 1-5; excessive salivation, local pain and tinnitus on 1-4; xerostomia and trismus on 1-3 and taste alteration 1-2; while Grade '0' denoting absence of symptom except tinnitus in which grade 1 means absence of symptom. Lower scale denotes less severity of the symptoms.

b. Assessment of performance status using Karnofsky score (Grading for well-being on 0 to 100 scale, higher score denotes better performance) and weight.

c. Assessment of Quality of Life (QoL) using Questionnaire QLQ C30 (designed for all types of cancers) and H&N35 (specially designed for oral cancer patients) of EORTC determined on the basis of patients' own perspective about well being.

d. QLQ C30 can be interpreted as—

1. Symptomatology (Symptom score)

2. Ability to perform routine activities (Functional score)

3. Overall well-being (Global score)

CTCAE, Karnofsky score and scoring for QoL are internationally accepted means of scoring symptoms and quality of life for cancer patients used in various studies in clinical trials.

B. Laboratory Investigations:

To support the clinical observations, additional studies were conducted using clinical laboratory investigations and basic laboratory investigations as follows:

Clinical Laboratory investigations: These investigations were conducted for assessing haemoglobin status and various cell types in peripheral blood. Toxicity for liver and kidney was assessed on the basis of corresponding enzyme levels. CRP levels were assessed as an indicator of initiation of inflammatory response. The tests performed were Haemogram, LFT (Liver Function Test), KFT (Kidney Function Test), CRP (C-reactive protein test).

Basic Laboratory Investigations:

These tests were carried out to assess status of oxidative stress and immunomodulatory effects in these patients. Reduction in oxidative stress was measured by estimating two enzymes viz., Super oxide dismutase (SOD) and Catalase and one protein Glutathione using commercial kits for biochemical methods. Pro inflammatory cytokines viz., IL-1$\beta$, IL-6, IL-8 and IL-10 were measured by ELISA method, using commercial kits for assessment of immunological status.

Assessment of Data:

The data for biochemical investigations was represented as mean of absolute values at each time point while for adverse effects, basic laboratory parameters, Karnofsky score, weight and QLQ assessment, data was analyzed as fold change in a given parameter compared to its level at time point A. In addition, for adverse effects the data was also analyzed based on the percentage and number of patients with varied severity levels of adverse effects at each time point. For symptoms, Mann Whitney 'Z' test, while for scores and laboratory investigations paired 't' test were applied.

Alleviation of Adverse Effects (Symptoms) of Radiotherapy in Oral Cancer Patients Using Polyherbal Metallo-Mineral Pharmaceutical Kit of the Present Disclosure Out of commonly observed adverse effects, nine significant symptoms were recorded in this study. The mean of gradation at each time point was recorded for both the groups. The observations for each group were compared with respective time point A and fold change histograms were plotted (FIG. 1A to FIG. 3A). Status of symptoms at time point A was also plotted as baseline.

In second group of histograms (FIG. 1B to FIG. 3B), percentage and number of patients in no/low degree of adverse effects (grade 0 and 1 of symptoms together) and higher degree of adverse effects (grade 2, 3, 4 and 5 of symptoms together) were represented in both the groups at various time points.

Results i. Stomatitis, Xerostomia and Taste Alteration—

Figure 1B:
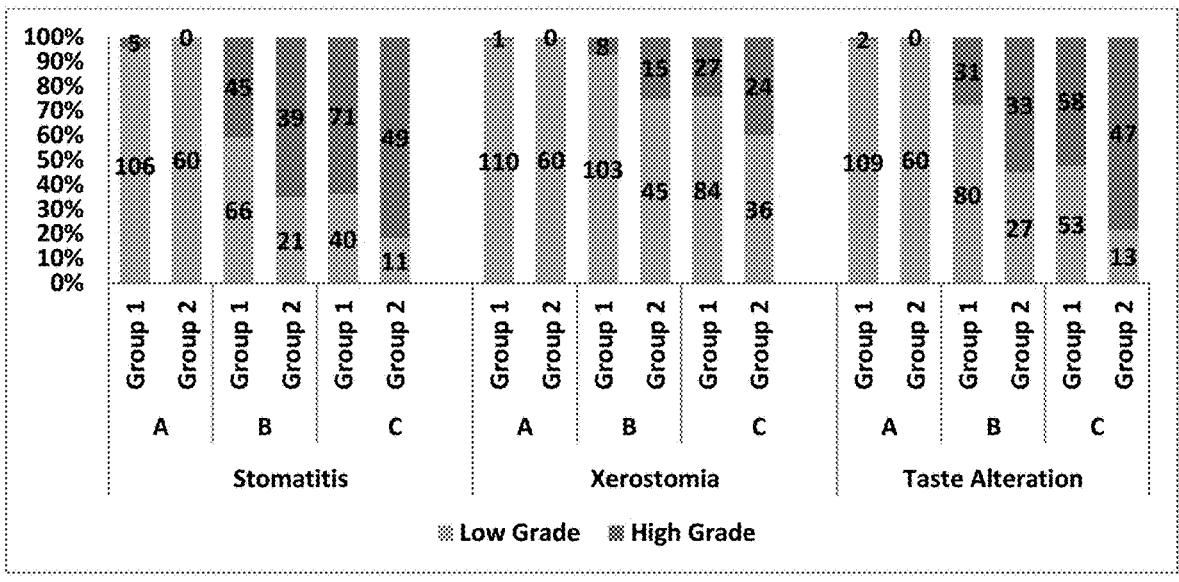
FIG. 1B depicts the adverse effects as stomatitis, xerostomia and taste alteration and is represented between percentage and number of patients. A Low degree adverse effect and High degree adverse effect is denoted by colour variation.

Control group (Group 2) shows significant increase in stomatitis, xerostomia and taste alteration as compared to the Study group (Group 1) during the period of radiotherapy (time points—B and C) as shown in FIG. 1A. Stomatitis and taste alteration showed extremely significant p values of (p<0.0001) at time points B and C, while xerostomia had highly significant p values of (p=0.001) and (p=0.006) at the time points B and C, respectively. FIG. 1B shows that at B and C time points, more number of patients from Control group suffered from higher grade of stomatitis, xerostomia and taste alteration than that of the Study group.

ii. Excessive Salivation, Trismus, Dysphagia—

Figure 2A:
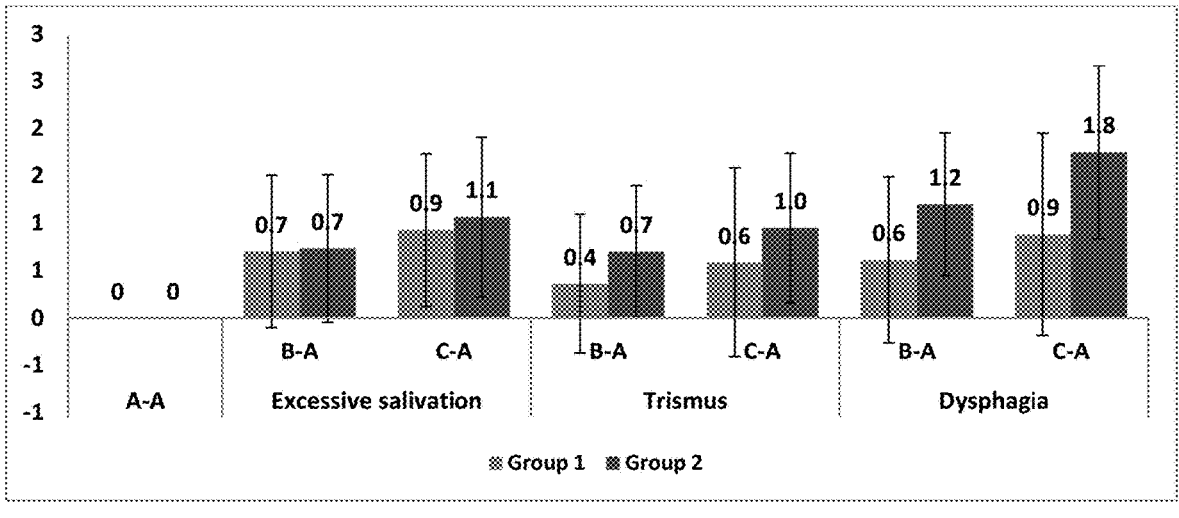
FIG. 2A depicts the clinical investigation for excessive salivation, trismus and dysphasia, in Study group and Control group wherein Study group denoted by Group 1' and Control group denoted by 'Group 2'.
Figure 2B:
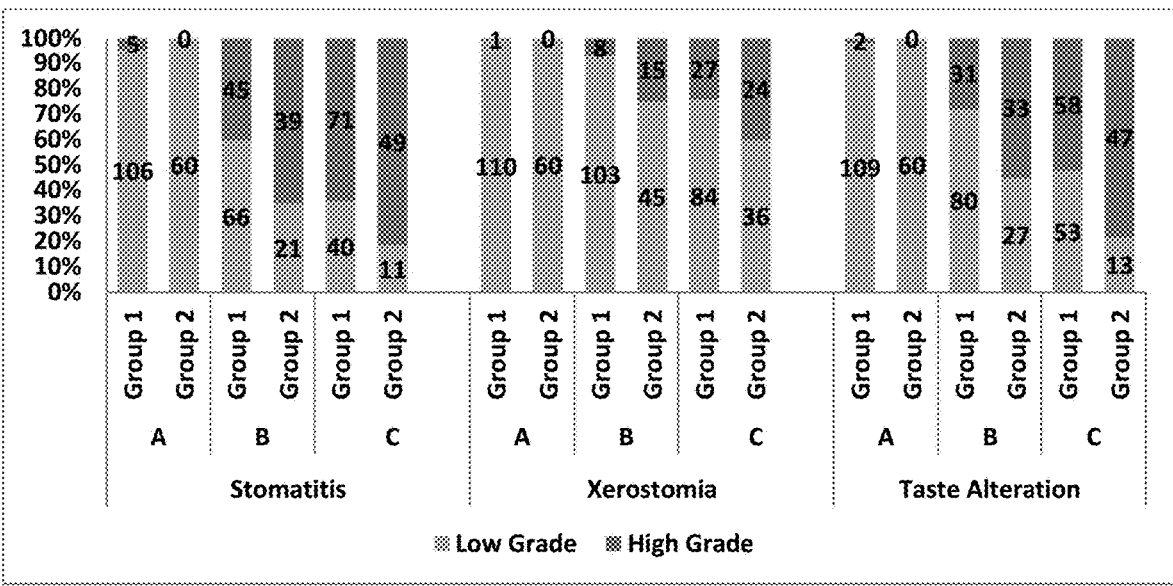
FIG. 2B depicts the adverse effects as excessive salivation, trismus and dysphasia and is represented between percentage and number of patients. A Low degree adverse effect and High degree adverse effect is denoted by colour variation.

Excessive salivation did not show significant difference in both, the Control (Group 2) and Study group (Group 1). However, trismus and dysphagia are much pronounced in Control group compared to study group patients in terms of fold change during the radiation period (FIG. 2A). Dysphagia showed extremely significant p value (p<0.0001)) at both the time points B and C, while trismus showed highly significant (p=0.005) and significant (p=0.02) p values at time points B and C, respectively. As can be seen from FIG. 2B, in case of excessive salivation at time point C, more number of patients suffered from higher grade of symptom in Control group as compared to the Study group. In case of trismus and dysphagia, number of patients in higher grade symptom in Control group increased rapidly at both the time points as compared to the increase in the Study group with respect to that at original time point A. Moreover, in Control group, nearly 50% and 85% patients had much severe adverse effect of dysphagia at time point B and C, respectively, compared to that in the Study group.

iii. Nausea, Local Pain, Tinnitus—

Figure 3A:
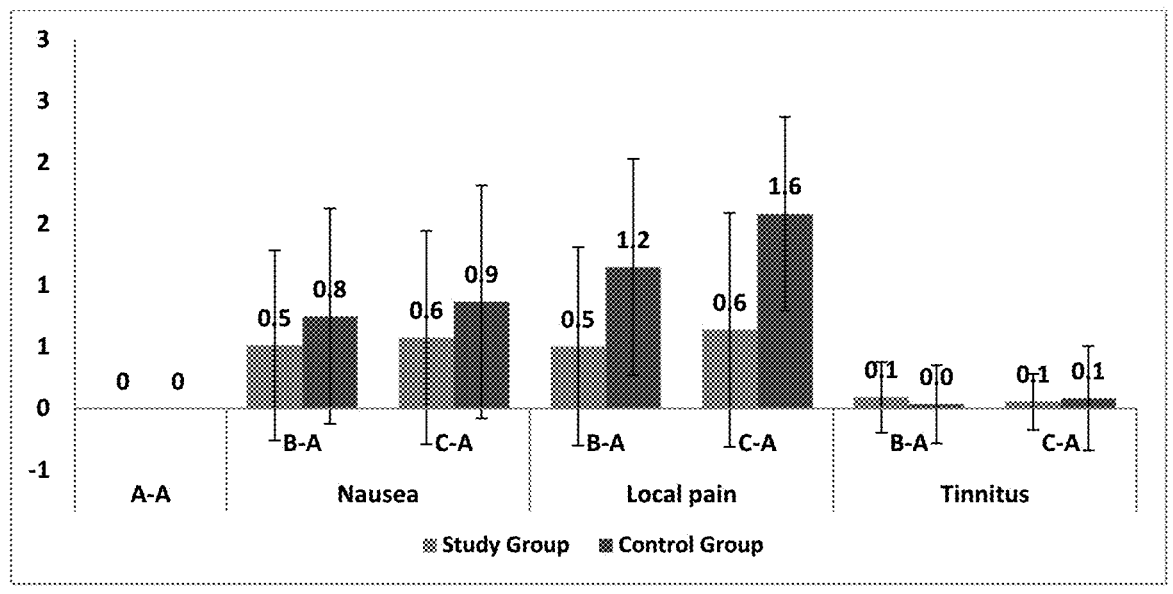
FIG. 3A depicts the clinical investigation for nausea, local pain and tinnitus in Study group and Control group.
Figure 3B:
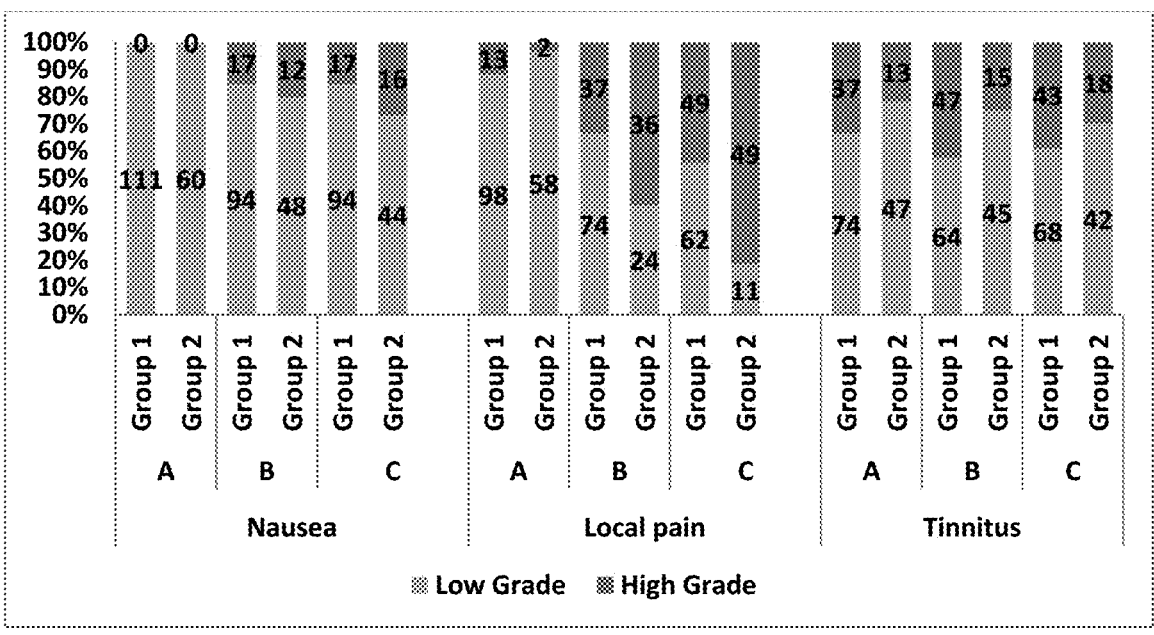
FIG. 3B depicts adverse effects as nausea, local pain and tinnitus as fold change and is represented between percentage and number of patients. A Low degree adverse effect and High degree adverse effect is denoted by colour variation.

Nausea was much less in Study group (Group 1) at both the time points B and C than the Control group (Group 2). However, it showed significant p value (p=0.04) at time point C only. Local pain was extremely less (p<0.0001) in the Study group at both the time points B and C as compared to Control group. Tinnitus did not show significant difference in both the groups (FIG. 3A). As seen from FIG. 3B nausea and tinnitus did not show any difference in symptom gradation at any time point. In case of local pain more number of patients of Control group were in higher grade of symptoms at time point B and C (approximately 60% and 80%, respectively) as compared to the Study group. Moreover, number of patients in higher grade symptom in Control group increased rapidly at both the time points as compared to the increase in the Study group with respect to that at original time point A.

Haematological and Biochemical Parameters in Oral Cancer Patients Using Polyherbal Metallo-Mineral Pharmaceutical Kit of the Present Disclosure The clinical laboratory parameters studied were Haemogram, LFT, KFT and CRP and found to be within normal range. Given below are the trends of differences between study and control groups. The results are based on mean values at each time point.

Results

Figure 4:
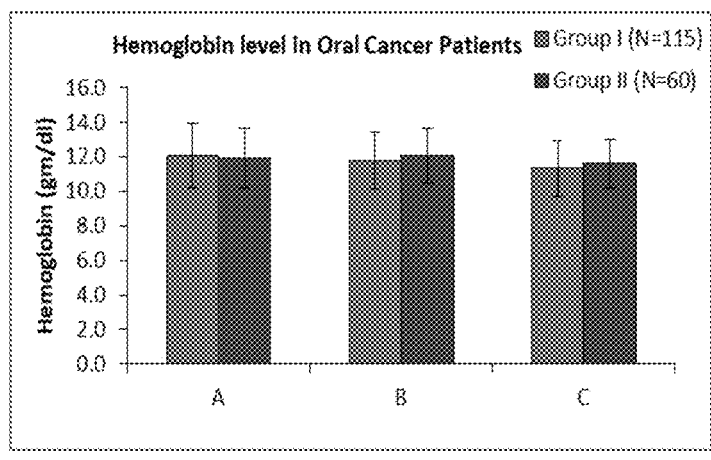
FIG. 4 depicts a graphical representation of effects of radiotherapy on hemoglobin level of Study group denoted by 'Group I' and Control group denoted by 'Group II' at time points A, B and C.

Haemoglobin—Haemoglobin remains unchanged during radiotherapy in both the groups (FIG. 4).

Figure 5:
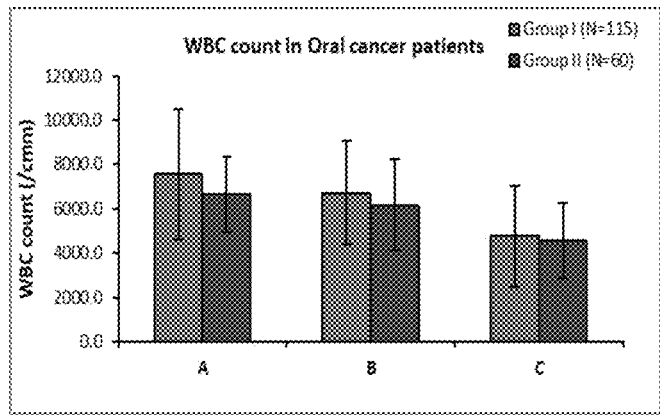
FIG. 5 depicts a graphical representation of effects of radiotherapy on white blood cell (WBC) count of Study group denoted by 'Group I' and Control group denoted by 'Group II' at time points A, B and C.
Figure 6:
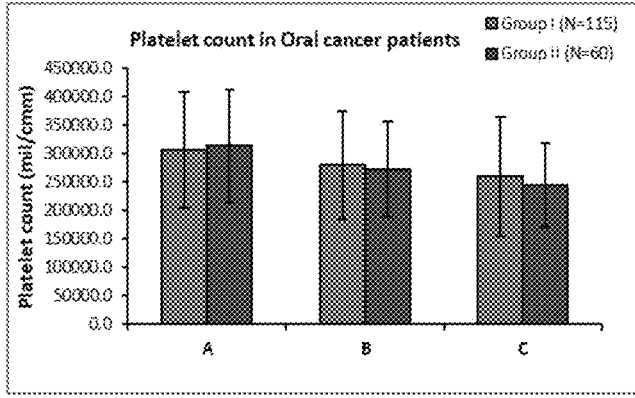
FIG. 6 depicts a graphical representation of effects of radiotherapy on platelet count of Study group denoted by 'Group I' and Control group denoted by 'Group II' at time points A, B and C.
Figure 7:
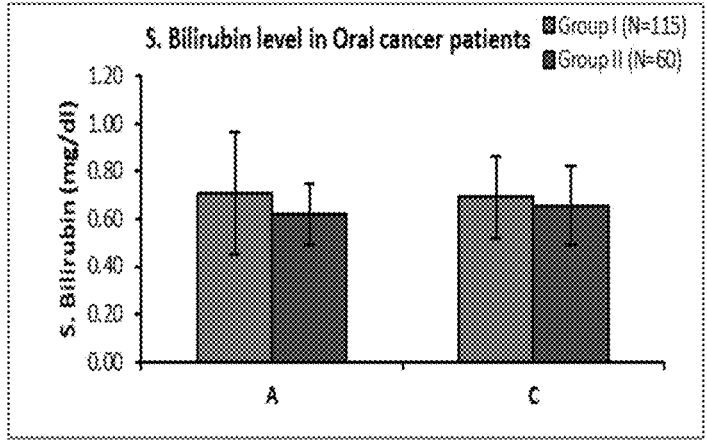
FIG. 7 depicts a graphical representation of effects of radiotherapy on Serum Bilirubin level of Study group denoted by 'Group I' and Control group denoted by 'Group II' at time points A and C.
Figure 8:
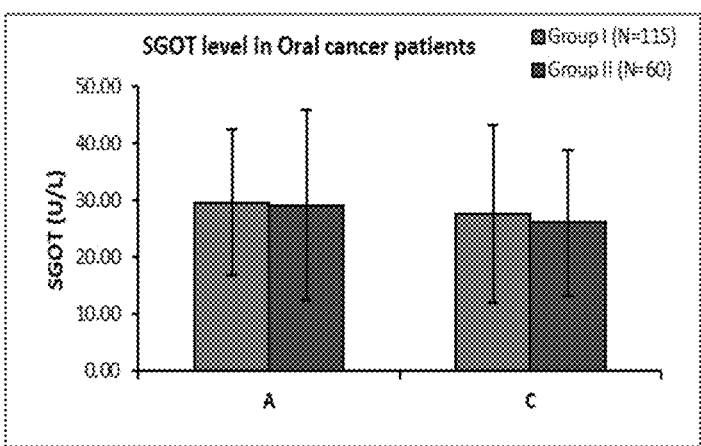
FIG. 8 depicts a graphical representation of effects of radiotherapy on SGOT level of Study group denoted by 'Group I' and Control group denoted by 'Group II' at time points A and C.
Figure 9:
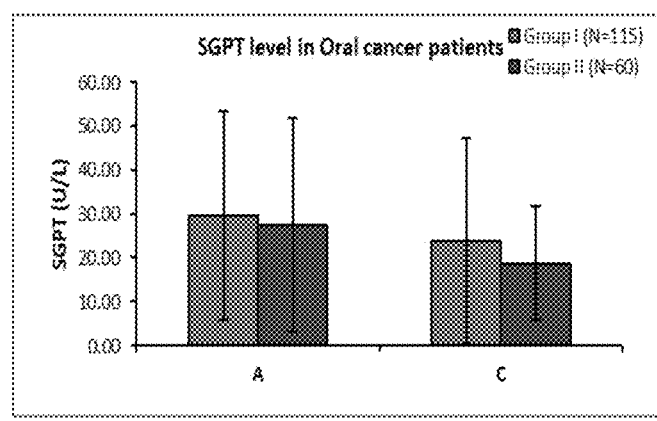
FIG. 9 depicts a graphical representation of effects of radiotherapy on SGPT level of Study group denoted by 'Group I' and Control group denoted by 'Group II' at time points A and C.
Figure 10:
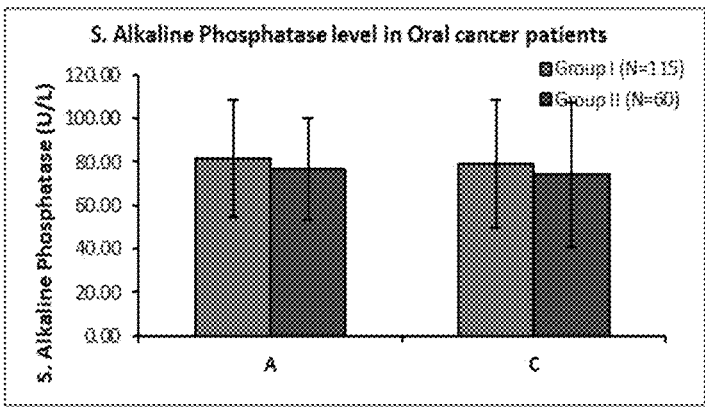
FIG. 10 depicts a graphical representation of effects of radiotherapy on Serum Alkaline phosphatase level of Study group denoted by 'Group I' and Control group denoted by 'Group II' at time points A and C.

WBCs and Platelets—WBCs and platelet count decreased slightly at the end of radiotherapy in both the groups (FIG. 5 and FIG. 6).

S. Bilirubin, SGPT, SGOT and Alkaline phosphatase—S. Bilirubin, SGPT, SGOT and Alkaline phosphatase levels were within normal range in both the groups throughout the study (FIG. 7, 8, 9 and FIG. 10).

Figure 11:
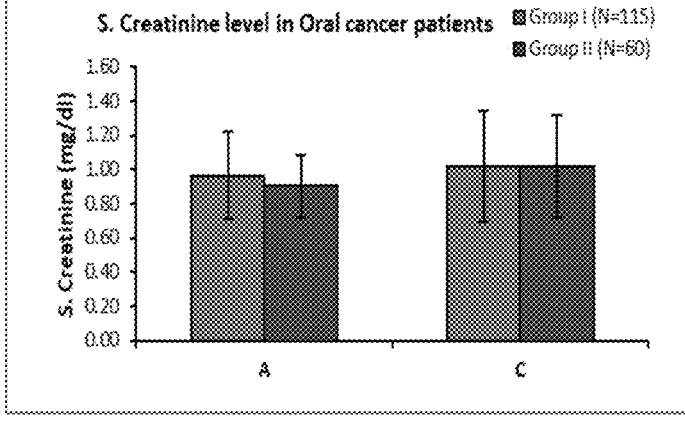
FIG. 11 depicts a graphical representation of effects of radiotherapy on Serum Creatinine level of Study group denoted by 'Group I' and Control group denoted by 'Group II' at time points A and C.

Serum Creatinine—S. Creatinine levels were within normal range in both the groups throughout the study (FIG. 11).

The above results clearly indicate non-toxicity of the polyherbal metallo-mineral pharmaceutical kit to liver and kidney functions.

Figure 12:
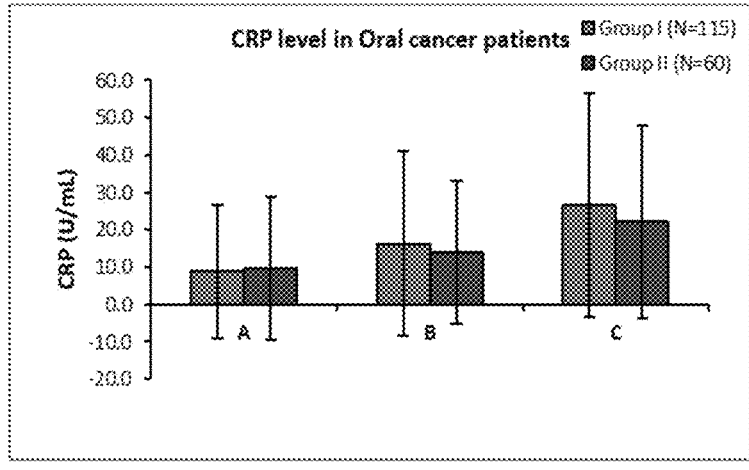
FIG. 12 depicts a graphical representation of effects of radiotherapy on C—reactive protein (CRP) level of Study group denoted by 'Group I' and Control group denoted by 'Group II' at time points A and C.

CRP—CRP level was comparable before commencement of radiotherapy and increased during radiotherapy in both the groups. The increase was higher in Study group (Group 1) than that of Control group (Group 2) although not significant (FIG. 12).

Studies on Immunomodulatory and Anti-Oxidant Markers Using Polyherbal Metallo-Mineral Pharmaceutical Kit of the Present Disclosure Immunomodulatory markers: Levels of cytokines IL-1β, IL-6, IL-8, and IL-10 were assessed to see the pro-inflammatory response caused by radiotherapy. The levels were represented in the form of fold increase at respective time points.

Figure 13:
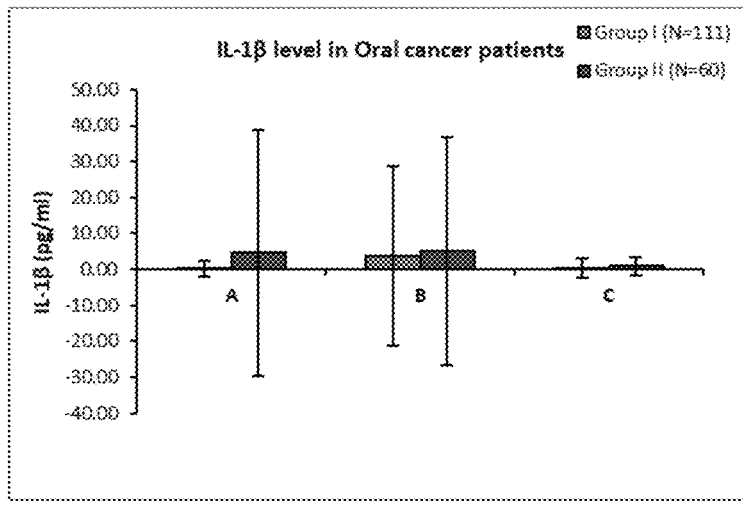
FIG. 13 depicts a graphical representation of effects of radiotherapy on Interleukine-1β (IL-1β) level as fold change in Study group denoted by 'Group I' and Control group denoted by 'Group II' at time points A and C.
Figure 14:
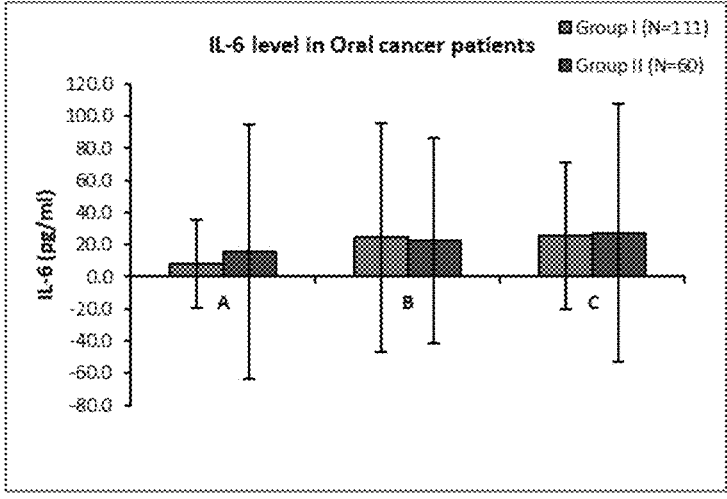
FIG. 14 depicts a graphical representation of effects of radiotherapy on Interleukine-6 (IL-6) level as fold change in Study group denoted by 'Group I' and Control group denoted by 'Group II' at time points A and C.
Figure 15:
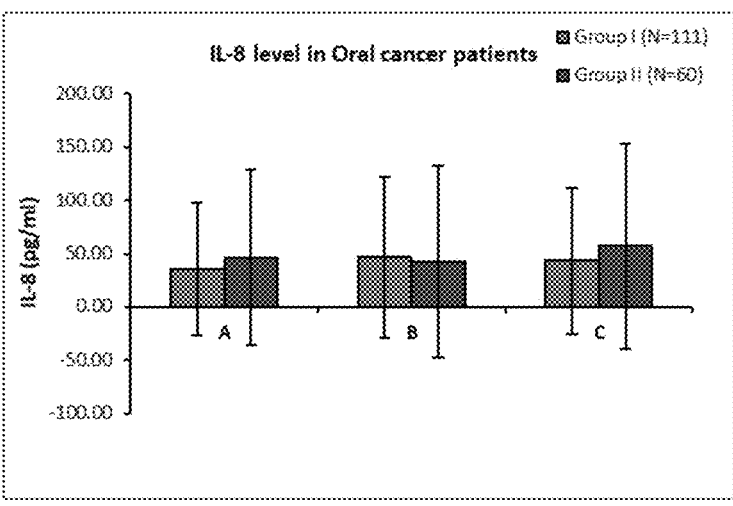
FIG. 15 depicts a graphical representation of effects of radiotherapy on Interleukine-8 (IL-8) level as fold change in Study group denoted by 'Group I' and Control group denoted by 'Group II' at time points A and C.
Figure 16:
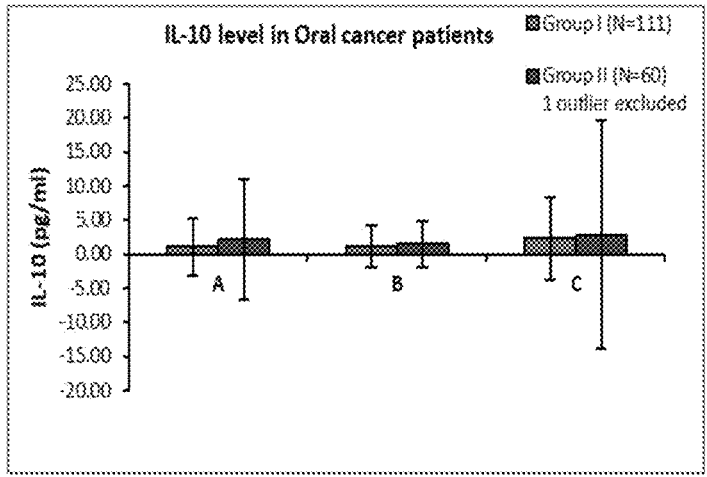
FIG. 16 depicts a graphical representation of effects of radiotherapy on Interleukine-10 (IL-10) level as fold change in Study group denoted by 'Group I' and Control group denoted by 'Group II' at time points A and C.

Serum levels of IL-1β did not show any significant change in both Study and Control groups (FIG. 13). It was observed that IL-6 levels increased in both the groups till mid of radiation; however, it remained unchanged at the end of radiation in both the groups (FIG. 14). IL-8 levels in Study group (Group 1) did not change during radiation, however, in Control group (Group 2) IL-8 showed increasing trend (FIG. 15). Serum IL-10 levels showed increasing trend in both Study and Control groups (FIG. 16).

Figure 17:
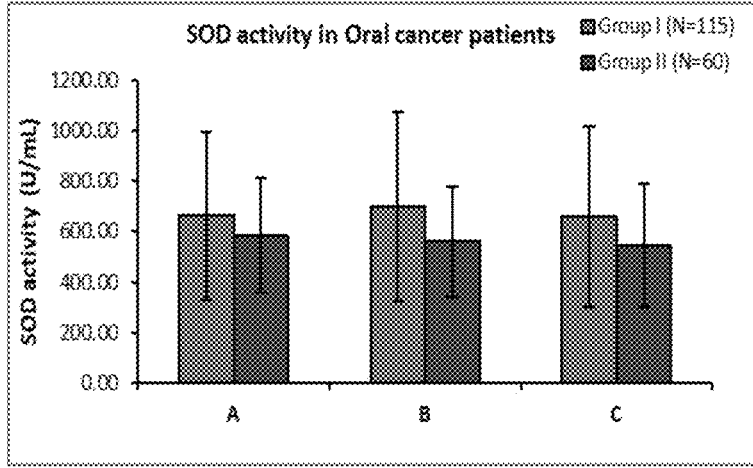
FIG. 17 depicts a graphical representation of effects of radiotherapy on Superoxide dismutase (SOD) activity as fold change in Study group denoted by 'Group I' and Control group denoted by 'Group II' at time points A and C.
Figure 18:
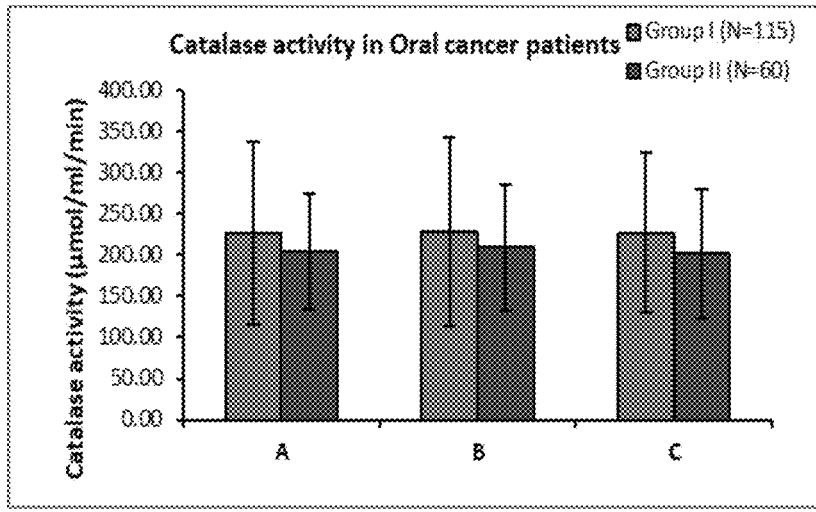
FIG. 18 depicts a graphical representation of effects of radiotherapy on catalase activity as fold change in Study group and Control group at time points A and C.
Figure 19:
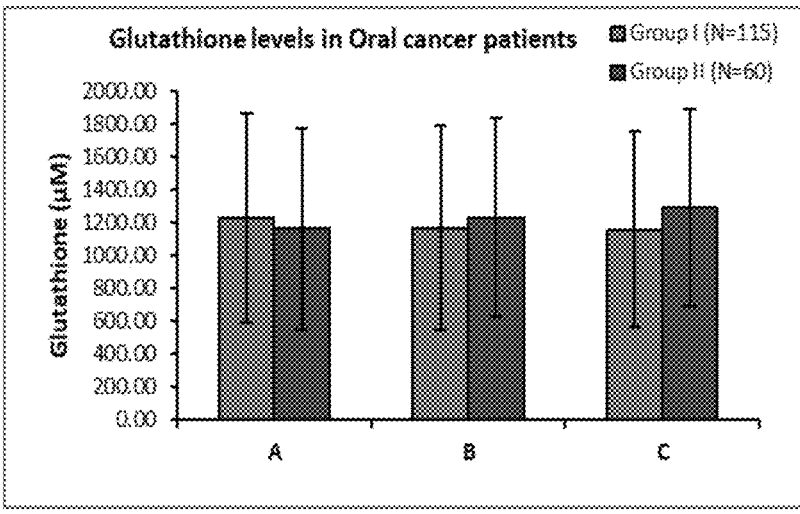
FIG. 19 depicts a graphical representation of effects of radiotherapy on glutathione level as fold change in Study group denoted by 'Group I' and Control group denoted by 'Group II' at time points A and C.

Oxidative Stress markers: It was seen that, SOD and catalase activities remained unchanged in both the groups. However, they were higher in Study group (Group 1) as compared to the Control group (Group 2) at all the time points (FIGS. 17 and 18, respectively). Glutathione, at time points B and C, decreased slightly in the Study group whereas, increased in Control group during progression of radiotherapy (FIG. 19). From FIG. 17 to 19, it is evident that dis-mutation of Reactive Oxygen Species i.e., superoxide ($O^{2-}$) into hydrogen peroxide and later decomposition to oxygen are efficient in the Study group due to the use of the polyherbal metallo-mineral pharmaceutical kit as compared to the Control group. It is further confirmed by increased levels of Glutathione in the Control group as compared to the Study group.

Figure 20:
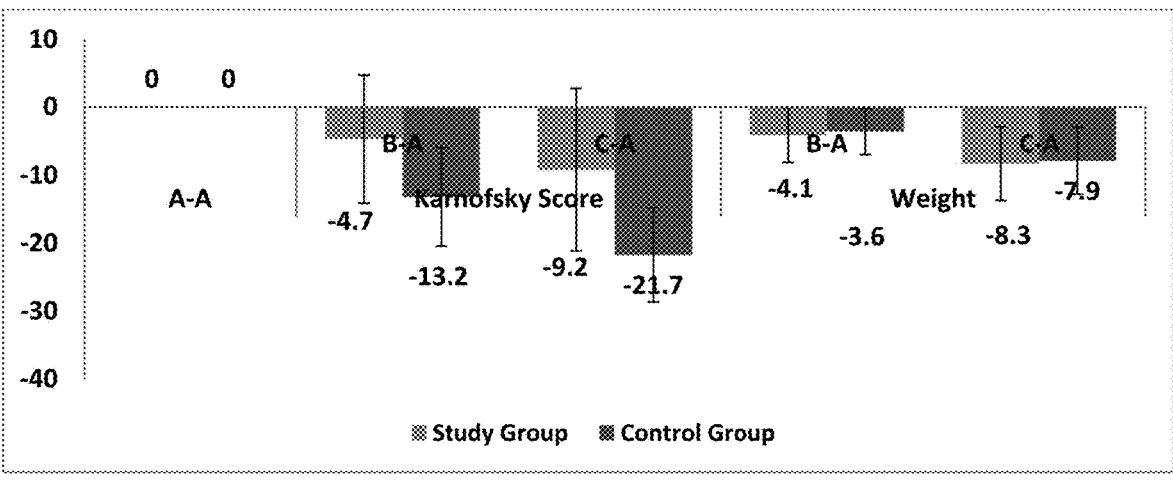
FIG. 20 depicts the clinical investigation for fold change of Karnofsky score and weight in Study group and Control group.

Assessment of Quality of Life (QoL) During Radiotherapy Using Polyherbal Metallo-Mineral Pharmaceutical Kit of the Present Disclosure Karnofsky score and weight—Karnofsky score and weight were represented as the mean values at each time point both the groups. These values were represented as percentile fold change. Control group (Group 2) showed significant reduction (p<0.0001) in the Karnofsky score at time point B and C and compared to the Study group (Group 1) whereas weight did not show any change at any of the time points in both the groups (FIG. 20).

Figure 21:
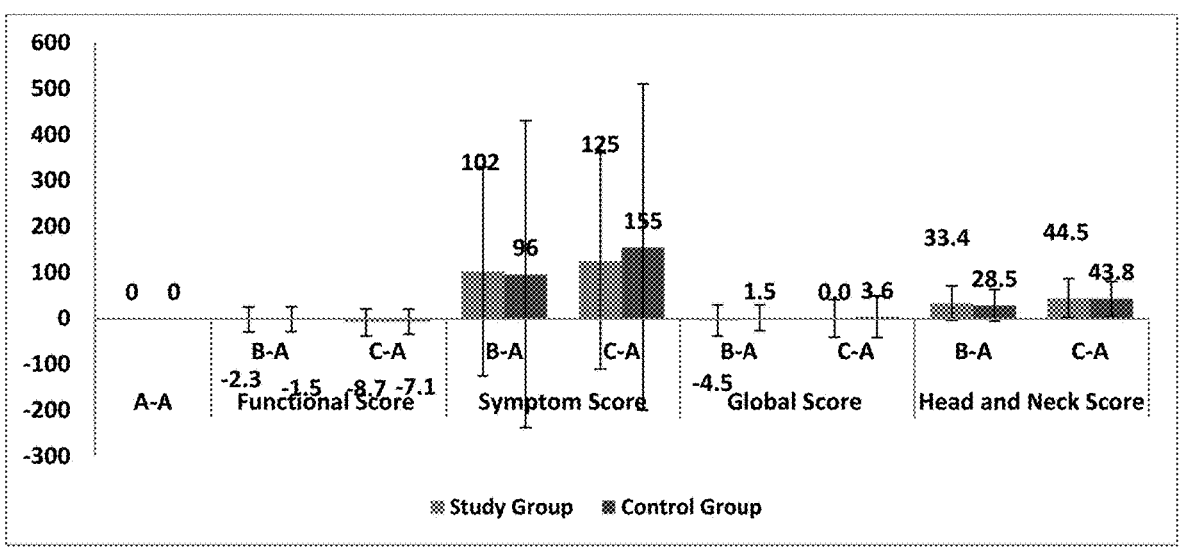
FIG. 21 depicts a graphical representation for fold change in Functional score, symptom score, global score and head & neck score in Study group and Control group.

QLQ scores—These scores were calculated as mean values and represented as percentile fold change at each time point for both the groups. Quality of life scores did not show significant difference in both the groups at any time point (FIG. 21).

Assessment Based on Case Reports During Radiotherapy Using Polyherbal Metallo-Mineral Pharmaceutical Kit of the Present Disclosure Case Reports of two patients matched for age, stage and grade, one treated with the polyherbal metallo-mineral pharmaceutical kit of the present disclosure (case report 1) and one not treated with the polyherbal metallo-mineral pharmaceutical kit of the present disclosure (case report 2)]

Nine symptoms viz., stomatitis, xerostomia, taste alteration, excessive salivation, trismus, dysphagia, nausea, local pain and tinnitus were assessed in both the case reports along with weight, Karnofsky score and QLQ. The assessment time points and the remaining outcome measures for both the case studies are similar to those as explained in example 8.

Case Report 1:

Patient Information:

Age at diagnosis: 70 yrs

Diagnosis: CA Left Buccal Mucosa

Status at enrollment: Post Surgery

Date of diagnosis: Jul. 7, 2017

Histopathology report: Infiltrating well differentiated Keratinizing Squamous Cell Carcinoma (SCC)

Stage: IVA

Grade: II

Past medical/surgical history: Facial Palsy in 2015

Treatment Details—

Surgery: Left segmental mandibulectomy+Wide Local Excision of Left Cheek+Left Supraomohyoid Neck Dissection done on Aug. 30, 2017.

Radiotherapy details: 30 #of radiotherapy taken to left face and neck from Oct. 4, 2017 to Nov. 15, 2017.

Results

1. Radiotherapy Side Effects—

Figure 22:
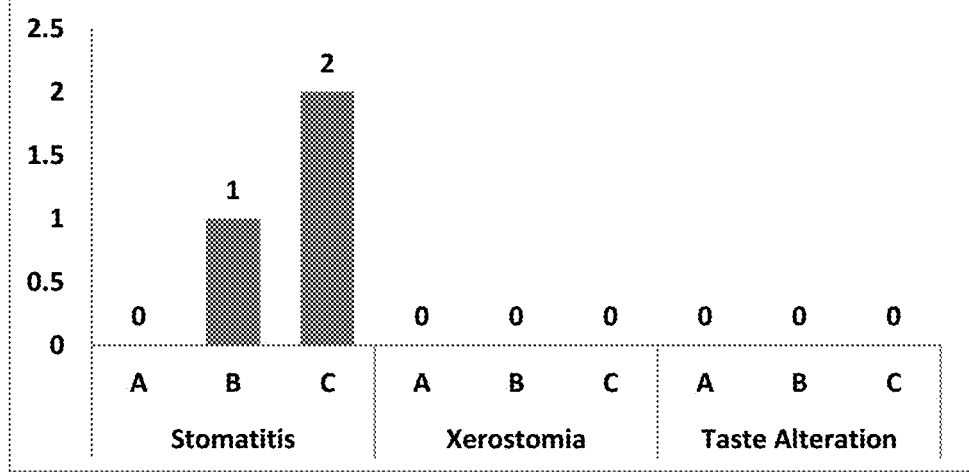
FIG. 22 depicts a graphical representation of effects of radiotherapy on stomatitis, xerostomia and taste alteration on the patient described in case report 1.
Figure 23:
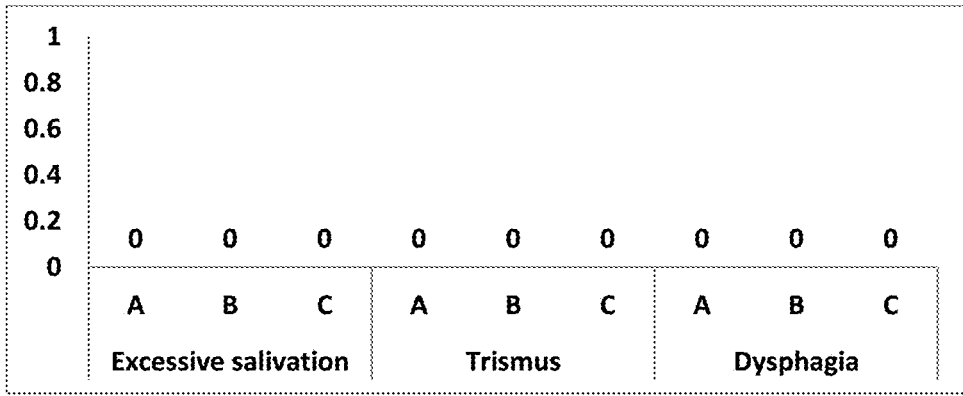
FIG. 23 depicts a graphical representation of no effects of radiotherapy on excessive salivation, trismus and dysphasia on the patient described in case report 1. The gradation of symptom at time points A, B and C is 0 as the patients do not show any of the above side effects.

The observations were compared with respective time point A and fold change histograms were plotted. From the FIGS. 22, 23 and FIG. 24, it is seen that patient never suffered by adverse effects like xerostomia, taste alteration, excessive salivation, trismus, dysphagia, tinnitus and nausea during the course of radiotherapy. FIG. 23 illustrates that the patient does not show any side effects like excessive salivation, trismus, dysphagia at time points A, B and C and thus shows 0.

Figure 24:
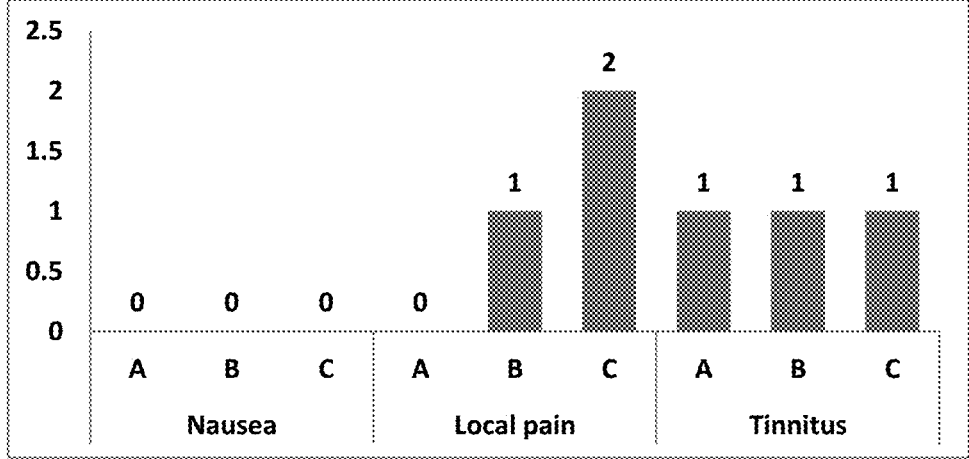
FIG. 24 depicts a graphical representation of effects of radiotherapy on nausea, local pain and tinnitus on the patient described in case report 1. The gradation of nausea at time points A, B and C is 0 as the patients do not show nausea as side effect.

FIG. 24 illustrates that the patient does not show nausea as a side effect at time points A, B and C thus shows 0.

The patient only showed stomatitis and local pain of grade 1 at B time point and grade 2 at the end of radiotherapy. These observations can be attributed to the adjunct oral treatment using the polyherbal metallo-mineral pharmaceutical kit of the present disclosure during radiotherapy.

2. Haematological and Biochemical Analysis—

TABLE 10

Data on haematological and biochemical investigations

| Time point | Hb *(12-16 g/dl) | WBC *(4000- 11000/cmm) | Platelet *(150000- 450000/cmm) | S. Bil. *(0-1.2 mg/dl) | SGOT *(0-31 U/L) | SGPT *(0-32 U/L) | S. Alkaline Phosphate *(44-147 U/L) | S. Creatinine *(0.7-1.7 mg/dl) | CRP *(0-6 mg/L) |
|---|---|---|---|---|---|---|---|---|---|
| A | 11.2 | 7300 | 251000 | 0.58 | 27 | 21.57 | 66.13 | 0.97 | 1.58 |
| B | 11.3 | 6500 | 264000 | ND | ND | ND | ND | ND | 2 |
| C | 11.1 | 6600 | 239000 | 0.55 | 28.35 | 12.3 | 44 | 1.17 | 6.27 |

*Denotes normal range of the respective parameter.
ND—Not Done
cmm—cubic millimeter From Table 10, it is evident that all the clinical laboratory parameters were in normal range at all time points.

Figure 25:
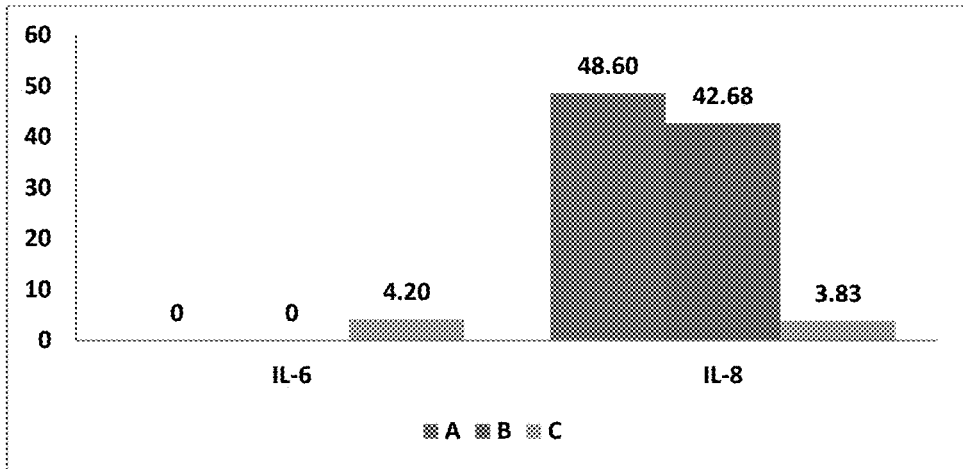
FIG. 25 depicts a graphical representation of effect of radiotherapy on IL-1β, IL-6, IL-8, and IL-10 levels in of the patient described in case report 1 at time points A, B and C.

3. Immune and Oxidative Stress Status:

Serum levels of IL-1β and IL-10 were below detectable level in this patient. Serum level of pro-inflammatory cytokine i.e., IL-6 were below detectable level before commencement of radiotherapy which increased at the end of radiation, though not significant. Serum level of anti-inflammatory cytokine i.e., IL-8 were higher in this patient before radiotherapy, further it showed decreasing trend at time point B but showed drastic decrease at the end of the treatment (FIG. 25).

Figure 26:
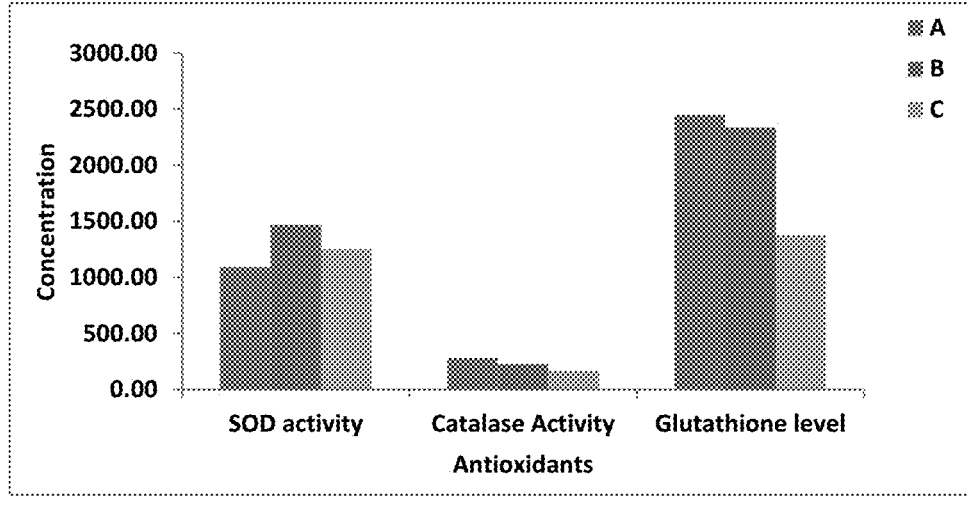
FIG. 26 depicts a graphical representation of effects of radiotherapy on SOD activity, catalase activity and glutathione level of the patient described in case report 1 at time points A, B and C.

It was observed that during the course, SOD activity increased till mid of radiation and decreased at the end of the treatment. However, Catalase activity and Glutathione levels showed decreasing trend in these patients (FIG. 26).

Figure 27:
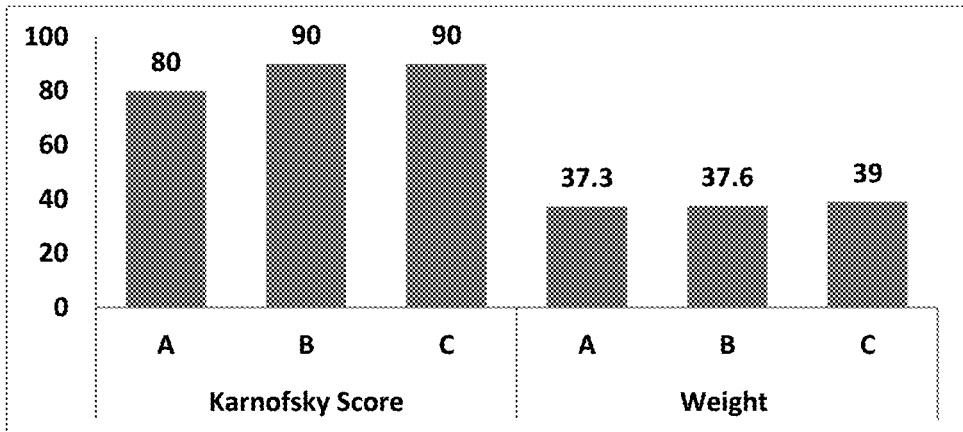
FIG. 27 depicts a graphical representation of effects of radiotherapy on Karnofsky score and weight of the patient described in case report.
Figure 28:
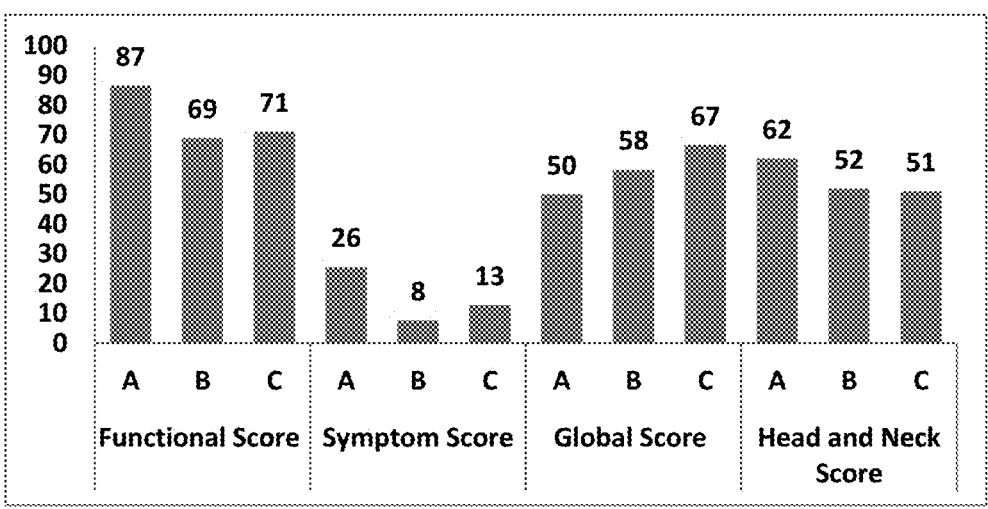
FIG. 28 depicts a graphical representation of effects of radiotherapy on Functional score, Symptom score, Global score and Head and neck score of QLQ of the patient described in case report 1.

4. Well-Being of Patient Recorded as Karnofsky Score, QoL Scores (Functional, Symptoms, Global Scores and Head and Neck Score) and Weight:

FIGS. 27 and 28 indicate the scores at time points A to C. Karnofsky and global scores showed continuous increase from time point A to C indicating improvement in quality of life. In case of functional score, functions decreased at time point B but increased at time point C. Weight remained stable throughout the period of observation while symptom score and head and neck score showed decreasing trend when compared with time point A during observational period. Overall quality of life and well-being appear to have improved which could be because of adjuvant treatment with oral polyherbal metallo-mineral pharmaceutical kit of the present disclosure.

Case Report 2:

Patient Information:

Age at diagnosis: 66 yrs

Diagnosis: Ca Right Lower Gingio-Buccal Sulcus

Status at enrollment: Post Surgery

Date of diagnosis: Feb. 3, 2018

Histopathology report: Well differentiated Squamous Cell Carcinoma (SCC)

Stage: IVA

Grade: I

Past medical/surgical history: Known case of Diabetes Mellitus, operated for leg and hand necrosis 15 yrs back.

Treatment Details—

Surgery: Mar. 8, 2018—Right segmental mandibulectomy with Lymph Node dissection and reconstruction.

Radiotherapy details: 30 #of radiotherapy taken to Bilateral face and neck from May 9, 2018 to Jun. 20, 2018.

Results

1. Radiotherapy Side Effects

Figure 29:
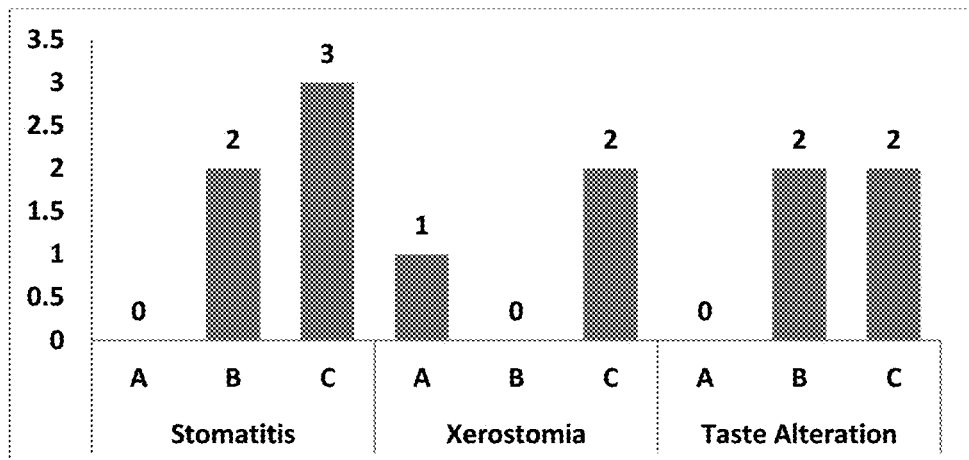
FIG. 29 depicts a graphical representation of effects of radiotherapy on stomatitis, xerostomia and taste alteration on the patient described in case report 2.
Figure 30:
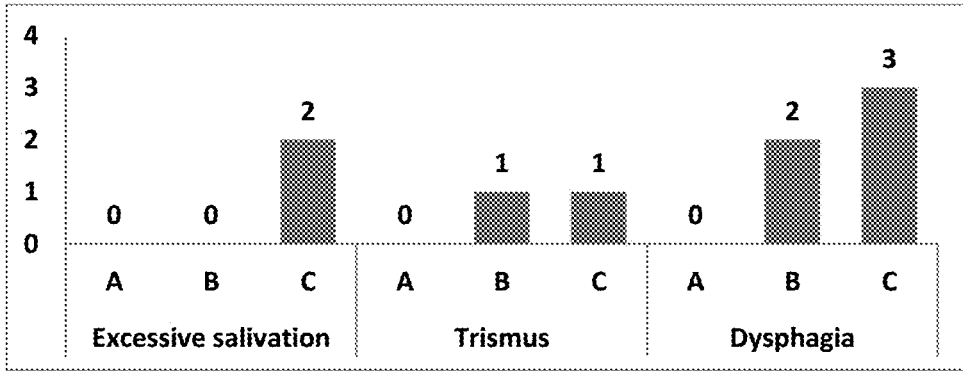
FIG. 30 depicts a graphical representation of effects of radiotherapy on excessive salivation, trismus and dysphagia on the patient described in case report 2.
Figure 31:
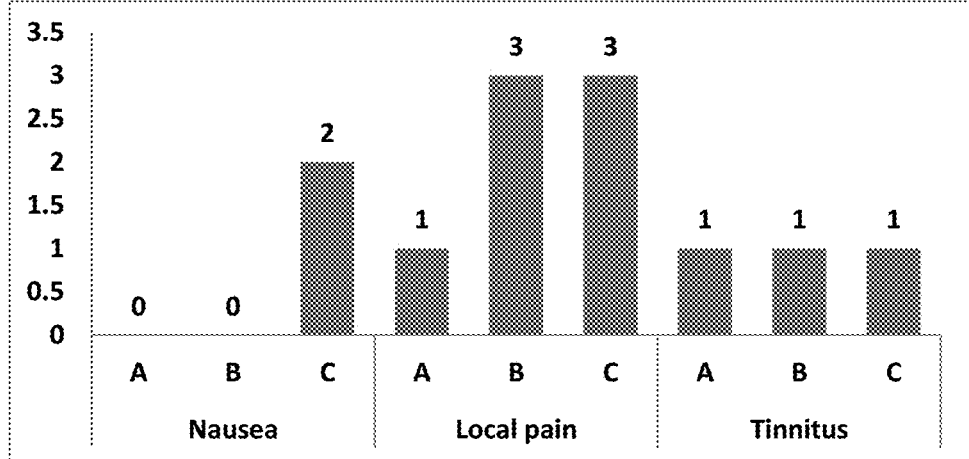
FIG. 31 depicts a graphical representation of effects of radiotherapy on nausea, local pain and tinnitus on the patient described in case report 2.

The observations were compared with respective time point A and fold change histograms were plotted. It can be seen from FIGS. 29, 30 and 31 that patient suffered from stomatitis, taste alteration, dysphagia with grade 2 at time point B. These symptoms increased till grade 3 in case of stomatitis and dysphagia while remained stable at grade 2 in case of taste alteration at time point C. Patient had local pain of grade 3 at both the time points B and C. Patient suffered from excessive salivation and nausea with grade 2 only at time point C which was not present at time point B. Patient had xerostomia before starting radiotherapy which subsided at time point B and again increased till grade 2 at time point C. Patient had trismus of grade 1 at both the time points B and C.

2. Haematological and Biochemical Analysis—

TABLE 11

Data on haematological and biochemical investigations

| Time point | Hb *(12-16 g/dl) | WBC *(4000- 11000/cmm) | Platelet *(150000- 450000/cmm) | S. Bil *(0-1.2 mg/dl) | SGOT *(0-31 U/L) | SGPT *(0-32 U/L) | S Alkaline Phosphates *(44-147 U/L) | S Creatinine *(0.7-1.7 mg/dl) | CRP *(0-6 mg/L) |
|---|---|---|---|---|---|---|---|---|---|
| A | 9.7 | 10300 | 489000 | 0.65 | 23.88 | 15.89 | 66 | 1.21 | 1.75 |
| B | 9.9 | 14600 | 528000 | ND | ND | ND | ND | ND | 6.8 |
| C | 11.2 | 8900 | 365000 | 0.62 | 26.2 | 15.18 | 64.46 | 1.29 | 24.92 |

ND—Not done
*Denotes normal range of respective parameter.

From Table 11, it is evident that the state of hemoglobin appears to increase during radiotherapy. The values of WBC and platelets are out of normal limits at time point A and B which came to normal range at time point C. LFT and KFT parameters are within normal range through out the treatment period. In case of CRP, it increased at time point B which showed drastic increase at time point C.

Figure 32:
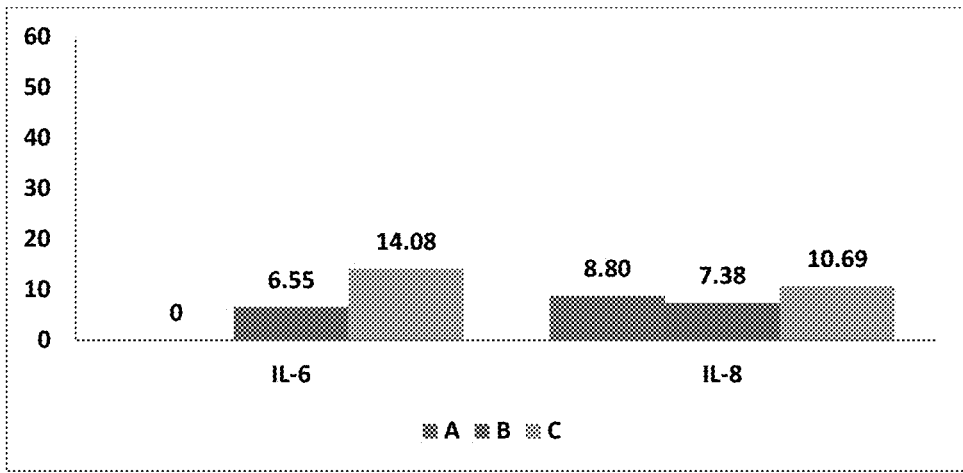
FIG. 32 depicts a graphical representation of effects of radiotherapy on IL-1β, IL-6, IL-8, and IL-10 levels of the patient described in case report 2 at time points A, B and C.
Figure 33:
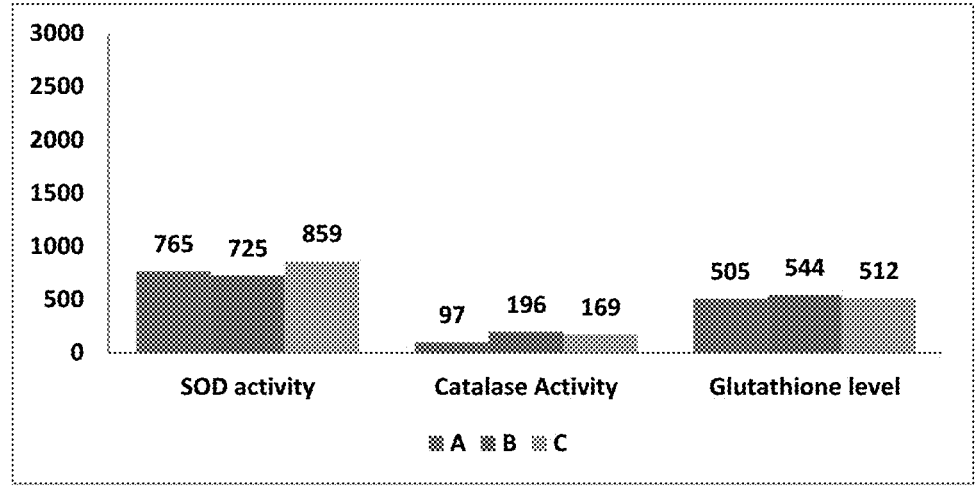
FIG. 33 depicts a graphical representation of effects of radiotherapy on SOD activity, catalase activity and glutathione level of the patient described in case report 2 at time points A, B and C.

3. Immune and Oxidative Stress Status:

Serum levels of IL-1$\beta$ and IL-10 were below detectable level in this patient. Serum level of pro-inflammatory cytokine i.e. IL-6 showed increasing trend while serum level of anti-inflammatory cytokine i.e. IL-8 remained unchanged till end of radiotherapy. It was observed that, SOD activity, catalase activity and Glutathione level remained unchanged in this patient (FIGS. 32 and 33).

Figure 34:
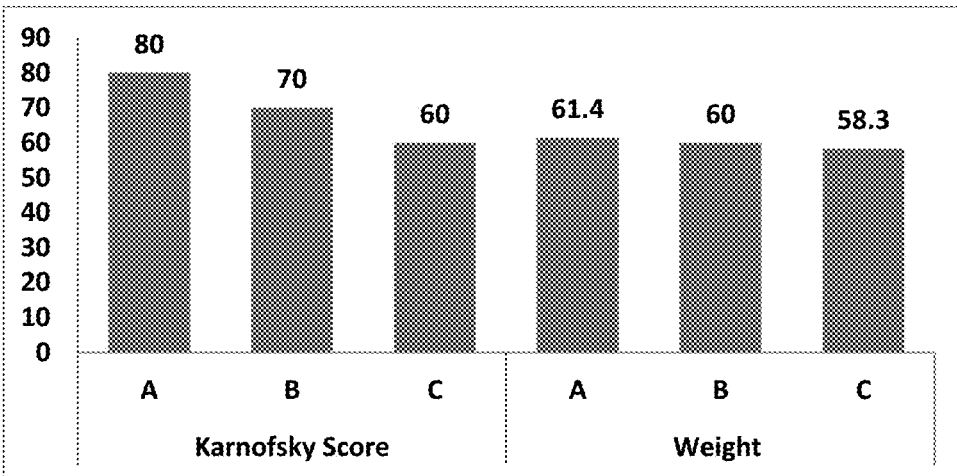
FIG. 34 depicts a graphical representation of effects of radiotherapy on Karnofsky score and weight of the patient described in case report 2.
Figure 35:
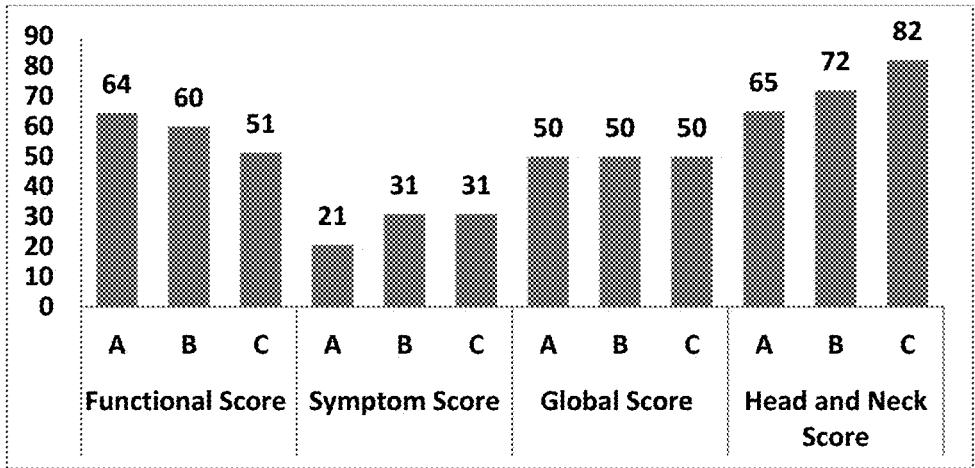
FIG. 35 depicts a graphical representation of effects of radiotherapy on Functional score, Symptom score, Global score and Head and neck score of QLQ of the patient described in case report 2.

4. Wellbeing of Patients Recorded as Karnofsky Score, QoL Scores (Functional, Symptoms, Global Scores and Breast Score) and Weight Karnofsky score reduced at time points B and C while weight remained almost constant throughout the period of observation (FIG. 34). Functional score decreased progressively up to time point C, while symptom score and head and neck scores showed upward trend till time point C. Global score remained stable till time point C (FIG. 35).

On comparison of two case reports, it was observed that adverse effects were higher in Case 2 at all the time points which were absent in Case 1 at those time points. These results show that intervention of the polyherbal metallo-mineral pharmaceutical kit of the present disclosure is favorable to the patient during the course of radiotherapy.

Overall, it is evident from the above examples that the polyherbal metallo-mineral pharmaceutical kit of the present disclosure reduces the adverse symptoms of radiotherapy such as stomatitis, dysphagia, nausea, trismus, xerostomia, excessive salivation, local pain and tinnitus in oral cancer patients leading to symptomatic relief to the patient.

It is further evident based on Karnofsky score, Functional score, Symptom score, Global score and head & neck score that the quality of life of the patients improved with the use of the polyherbal metallo-mineral pharmaceutical kit of the present disclosure. Also improvement in immune and oxidative status added to the betterment of the quality of life of the oral cancer patients.

Technical Advancements

The present disclosure described herein above has several technical advantages including, but not limited to, the realization of a polyherbal metallo-mineral pharmaceutical kit that:

reduces the adverse effects of radiotherapy such as stomatitis, xerostomia, taste alteration, excessive salivation, trismus, dysphagia, nausea, local pain and tinnitus;

produces enhanced anti-inflammatory, anti-oxidant and immunomodulatory effect; and improves the oral hygiene, quality of life and functional ability of the patients treated with radiotherapy.

The embodiments as described herein above, and various features and advantageous details thereof are explained with reference to the non-limiting embodiments in the description. Descriptions of well-known aspects, components, and molecular biology techniques are omitted so as to not unnecessarily obscure the embodiments herein.

The foregoing description of specific embodiments so fully reveal the general nature of the embodiments herein, that others can, by applying current knowledge, readily modify and/or adapt for various applications of such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein. Further, it is to be distinctly understood that the foregoing descriptive matter is to be interpreted merely as illustrative of the disclosure and not as a limitation.

Having described and illustrated the principles of the present disclosure with reference to the described embodiments, it will be recognized that the described embodiments can be modified in arrangement and detail without departing from the scope of such principles.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The invention claimed is:

1. A polyherbal metallo-mineral pharmaceutical kit, wherein said kit comprises:
   a. a first container containing Suvarna Bhasmadi Vati (SBV) in solid dosage form in an amount in the range of 800 mg/day to 1000 mg/day;
   b. a second container containing Mouktikyukta Kamdudha Vati (MKV) in solid dosage form in an amount in the range of 800 mg/day to 1200 mg/day;
   c. a third container containing Yashtimadhu Ghrut (YTG) in viscous dosage form in an amount in the range of 8 gm/day to 12 gm/day;
   d. a fourth container containing Ananta Vati (AV) in solid dosage form in an amount in the range of 0.5 gm/day to 2 gm/day;
   e. a fifth container containing Yashtimadhu Taila (YTO) in viscous oily dosage form in an amount in the range of 2 drop/day to 5 drops/day; and
   f. a sixth container containing Gandush Churna (GC) in coarse powder dosage form in an amount in the range of 3 gm/day to 10 gm/day, wherein said Gandush Churna (GC) comprises:
      coarse powder obtained from the pericarp of Haritaki in an amount ranging from 23 wt % to 34 wt % of the total weight of the said Gandush Churna (GC);
      coarse powder obtained from the pericarp of Bibhitaki in an amount ranging from 23 wt % to 34 wt % of the total weight of said Gandush Churna (GC);
      coarse powder obtained from the pericarp of Amalaki in an amount ranging from 23 wt % to 34 wt % of the total weight of said Gandush Churna (GC); and
      coarse powder obtained from the rhizome of Haridra in an amount ranging from 11 wt % to 17 wt % of the total weight of said Gandush Churna (GC),
   wherein each said container in said kit containing doses equivalent to 15 days to 6 weeks.

2. The kit as claimed in claim 1, wherein said Suvarna Bhasmadi Vati (SBV) comprises:
   Suvarna bhasma in an amount ranging from 2 wt % to 7 wt % of the total weight of the said Suvarna Bhasmadi Vati (SBV);

Mouktik bhasma in an amount ranging from 20 wt % to 35 wt % of the total weight of the said Suvarna Bhasmadi Vati (SBV);

Guduchi sattva in an amount ranging from 45 wt % to 60 wt % of the total weight of the said Suvarna Bhasmadi Vati (SBV); and at least one first excipient in an amount ranging from 5 wt % to 30 wt % of the total weight of the said Suvarna Bhasmadi Vati (SBV).

3. The kit as claimed in claim 1, wherein said Mouktikyukta Kamdudha Vati (MKV) comprises:

Mouktik bhasma in an amount ranging from 10 wt % to 14 wt % of the total weight of the said Mouktikyukta Kamdudha Vati (MKV);

Shankha bhasma in an amount ranging from 10 wt % to 14 wt % of the total weight of the said Mouktikyukta Kamdudha Vati (MKV);

Shouktik bhasma in an amount ranging from 10 wt % to 14 wt % of the total weight of the said Mouktikyukta Kamdudha Vati (MKV);

Kapardik bhasma in an amount ranging from 10 wt % to 14 wt % of the total weight of the said Mouktikyukta Kamdudha Vati (MKV);

Praval bhasma in an amount ranging from 10 wt % to 14 wt % of the total weight of the said Mouktikyukta Kamdudha Vati (MKV);

Guduchi sattva in an amount ranging from 10 wt % to 14 wt % of the total weight of the said Mouktikyukta Kamdudha Vati (MKV);

Shudhha Gairik in an amount ranging from 10 wt % to 14 wt % of the total weight of the said Mouktikyukta Kamdudha Vati (MKV); and at least one second excipient in an amount ranging from 10 wt % to 25 wt % of the total weight of the said Mouktikyukta Kamdudha Vati (MKV).

4. The kit as claimed in claim 1, wherein said Yashtimadhu Ghrut (YTG) comprises:

aqueous or alcoholic extract obtained from the stems and stolons of Yashtimadhu, wherein said extract is in an amount ranging from 2 wt % to 10 wt % of the total weight of said Yashtimadhu Ghrut (YTG); and Ghee in an amount ranging from 95 wt % to 98 wt % of the total weight of said Yashtimadhu Ghrut (YTG).

5. The kit as claimed in claim 1, wherein said Ananta Vati (AV) comprises:

powder obtained from dried roots of Ananta in an amount ranging from 75 wt % to 92 wt % of the total weight of said Ananta Vati (AV), wherein said powder has a particle size in the range of 150 to 180 microns; and at least one third excipient in an amount ranging from 8 wt % to 25 wt % of the total weight of said Ananta Vati (AV).

6. The kit as claimed in claim 1, wherein said Yashtimadhu Taila (YTO) comprises:

aqueous or alcoholic extract obtained from the stems and stolons of Yashtimadhu, wherein said extract is in amount ranging from 2 wt % to 10 wt % of the total weight of said Yashtimadhu Taila (YTO); and Sesame oil in an amount ranging from 95 wt % to 98 wt % of the total weight of said Yashtimadhu Taila (YTO).

7. The kit as claimed in claim 1, wherein said Gandush Churna (GC) is boiled in a predetermined amount of water for gargling.

8. The kit as claimed in any one of claim 2, wherein said first excipient is selected from the group consisting of gum acacia, guar gum, and xanthan gum.

9. The kit as claimed in claim 3, wherein said second excipient is selected from the group consisting of gum acacia, guar gum, and xanthan gum.

10. The kit as claimed in claim 5, wherein said third excipient is selected from the group consisting of gum acacia, guar gum, and xanthan gum.

11. A method of alleviating adverse effects of radiotherapy in oral cancer patients by using a polyherbal metallo-mineral pharmaceutical kit as claimed in claim 1, wherein said kit is administered as follows:

a. Suvarna Bhasmadi Vati (SBV) in solid dosage form in an amount in the range of 800 mg/day to 1000 mg/day;

b. Mouktikyukta Kamdudha Vati (MKV) in solid dosage form in an amount in the range of 800 mg/day to 1200 mg/day;

c. Yashtimadhu Ghrut (YTG) in viscous dosage form in an amount in the range of 8 gm/day to 12 gm/day;

d. Ananta Vati (AV) in solid dosage form in an amount in the range of 0.5 gm/day to 2 gm/day;

e. Yashtimadhu Taila (YTO) in viscous oily dosage form in an amount in the range of 2 drops/day to 5 drops/day; and f. Gandush Churna (GC) in coarse powder dosage form in an amount in the range of 3 gm/day to 10 gm/day.

12. The method as claimed in claim 11, wherein said Suvarna Bhasmadi Vati (SBV) is administered as 2 tablets twice a day;

said Mouktikyukta Kamdudha Vati (MKV) is administered as 2 tablets a day;

said Yashtimadhu Ghrut (YTG) is administered as 1 tsp twice a day and as 2 drops for local application;

said Ananta Vati (AV) is administered as 4 tablets per day; and said Yashtimadhu Taila (YTO) is administered as 2 drops for nasal application.

13. The kit as claimed in claim 7, wherein said Gandush Churna (GC) is administered as decoction for gargling.

* * * * *